US009561041B2

(12) United States Patent
Snider et al.

(10) Patent No.: US 9,561,041 B2
(45) Date of Patent: Feb. 7, 2017

(54) PATIENT SPECIFIC ALIGNMENT GUIDE FOR A PROXIMAL FEMUR

(75) Inventors: Ashley M. Snider, Memphis, TN (US); Bryan I. Nishimoto, Germantown, TN (US); Matthew J. Demmer, Memphis, TN (US); David Mehl, Memphis, TN (US); Timothy J. Bourne, Etobicoke, CA (US); James Gatewood, Memphis, TN (US); Phillip Frederick, Memphis, TN (US); Abraham B. Salehi, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1596 days.

(21) Appl. No.: 12/775,901

(22) Filed: May 7, 2010

(65) Prior Publication Data

US 2010/0286700 A1 Nov. 11, 2010

Related U.S. Application Data

(60) Provisional application No. 61/176,455, filed on May 7, 2009, provisional application No. 61/230,064, filed on Jul. 30, 2009.

(51) Int. Cl.
*A61B 17/17* (2006.01)

(52) U.S. Cl.
CPC ........ *A61B 17/175* (2013.01); *A61B 2034/105* (2016.02); *A61B 2034/108* (2016.02); *Y10T 29/49* (2015.01)

(58) Field of Classification Search
USPC .................... 606/53, 86 R, 87, 89
See application file for complete search history.

(56) References Cited

U.S. PATENT DOCUMENTS 5,098,383 A 3/1992 Hemmy
5,824,085 A 10/1998 Sahay
(Continued)

FOREIGN PATENT DOCUMENTS

GB 2442441 4/2008
WO WO9325157 12/1993
(Continued)

OTHER PUBLICATIONS

Brochure entitled smith&nephew Birmingham Hip Resurfacing Surgical Technique Addendum Quick Wire Femoral Alignment Jig, pp. 1-8 (2009).
(Continued)

*Primary Examiner* — Christian Sevilla
(74) *Attorney, Agent, or Firm* — Taft Stettinius & Hollister LLP

(57) ABSTRACT

An alignment guide for aligning instrumentation along a proximal femur includes a neck portion configured to wrap around a portion of the neck of the femur, a head underside portion configured to abut a disto-lateral portion of the femoral head and a medial head portion configured to overlie a medial portion of the head. Portions of the guide can have an inner surface generally a negative of the femoral bone of a specific patient that the guide overlies; such surfaces can be formed using data obtained from the specific patient. The neck portion can be configured to rotationally stabilize the guide by abutting and generating a first gripping force on the neck. The femoral head portions can be configured to grip the head portion of the femur and can support a bore guide that is configured to guide an instrument to the femur in a specified location and along a given axis.

20 Claims, 18 Drawing Sheets

(56) References Cited

U.S. PATENT DOCUMENTS

| | | | |
|---|---|---|---|
| 6,156,069 | A | 12/2000 | Amstutz |
| 6,259,943 | B1 | 7/2001 | Cosman |
| 6,595,999 | B2 | 7/2003 | Marchione |
| 6,712,856 | B1 | 3/2004 | Carignan |
| 6,905,514 | B2 | 6/2005 | Carignan |
| 7,534,263 | B2 | 5/2009 | Burdulis, Jr. et al. |
| 2003/0055502 | A1 | 3/2003 | Lang |
| 2003/0216669 | A1 | 11/2003 | Lang |
| 2004/0133276 | A1 | 7/2004 | Lang et al. |
| 2004/0138754 | A1 | 7/2004 | Lang |
| 2004/0204644 | A1 | 10/2004 | Tsougarakis |
| 2004/0236424 | A1 | 11/2004 | Berez et al. |
| 2005/0119664 | A1 | 6/2005 | Carignan |
| 2005/0148843 | A1 | 7/2005 | Roose |
| 2005/0234461 | A1 | 10/2005 | Burdulis, Jr. et al. |
| 2006/0122617 | A1 | 6/2006 | Lavalee |
| 2007/0198022 | A1 | 8/2007 | Lang et al. |
| 2008/0287954 | A1 | 11/2008 | Kunz et al. |
| 2008/0312659 | A1 | 12/2008 | Metzger et al. |
| 2009/0018546 | A1 | 1/2009 | Daley |
| 2009/0088760 | A1* | 4/2009 | Aram et al. ............. 606/87 |
| 2009/0088763 | A1* | 4/2009 | Aram et al. ............. 606/88 |
| 2009/0118736 | A1* | 5/2009 | Kreuzer ............. 606/96 |
| 2009/0222015 | A1 | 9/2009 | Park et al. |
| 2009/0222016 | A1 | 9/2009 | Park et al. |
| 2009/0254093 | A1 | 10/2009 | White et al. |
| 2010/0016986 | A1 | 1/2010 | Trabish |
| 2011/0015637 | A1 | 1/2011 | De Smedt et al. |

FOREIGN PATENT DOCUMENTS

| | | |
|---|---|---|
| WO | WO2007137327 | 12/2007 |
| WO | WO2008014618 | 2/2008 |
| WO | WO2009001109 | 12/2008 |
| WO | WO2009009660 | 1/2009 |
| WO | WO2010129870 | 11/2010 |

OTHER PUBLICATIONS

Brochure entitled smith&nephew Birmingham Hip Resurfacing System Surgical Technique, pp. 1-50 (2007).

Raaijmaakers, et al., "A custom-made guide-wire positioning device for Hip Surface Replacement Arthroplasty: description and first results," *BMC Musculoskeletal Disorders*, 11:161 (2010).

Radermacher, et al., "Computer Assisted Orthopaedic Surgery With Image Based Individual Templates," *Clinical Orthopaedics and Related Research*, 354:28-38 (1998).

Preliminary Amendment dated Aug. 6, 2009 in U.S. Appl. No. 12/171,083.

Office Action dated Feb. 11, 2011 in U.S. Appl. No. 12/171,083.

Response dated Apr. 28, 2011 in U.S. Appl. No. 12/171,083.

Office Action dated May 26, 2011 in U.S. Appl. No. 12/171,083.

International Search Report and Written Opinion dated Aug. 4, 2010 in related Application No. PCT/US2010/034043.

OtisMed Website Innovation in Motion www.otismed.com, 08 pages (2008).

Eckhoff, et al., "Three-Dimensional Mechanics, Kinematics and Morphology of the Knee Viewed in Virtual Reality," *The Journal of Bone and Joint Surgery* (American), 87:71-80 (2005).

European Patent Office, European Office Action, dated Oct. 13, 2015, 4 pages.

Canadian Patent Office, First Office Action dated Apr. 1, 2016, 4 pages.

European Examination Report (Second); European Patent Office; European Patent Application No. 10718014.3; Aug. 24, 2016; 4 pages.

Australian Examination Report No. 1; Australian Patent Office; Australian Patent Application No. 2016202434; Oct. 24, 2016; 3 pages.

\* cited by examiner

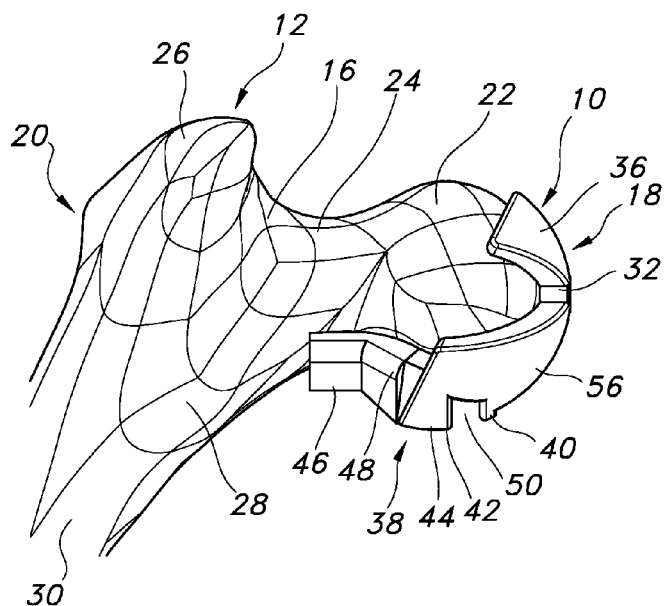
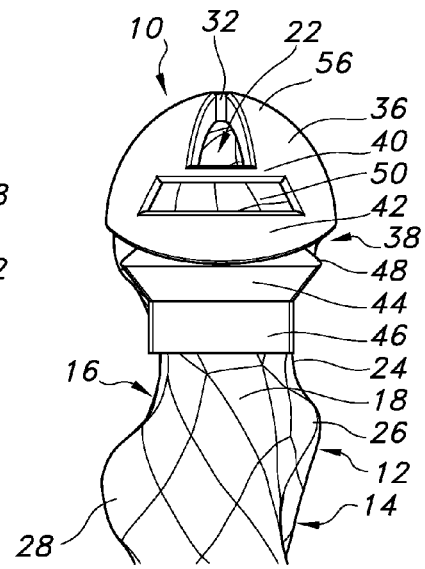
FIG. 1
FIG. 2
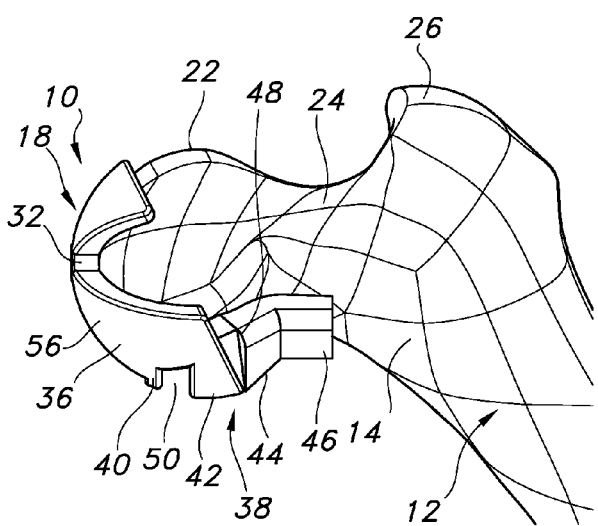
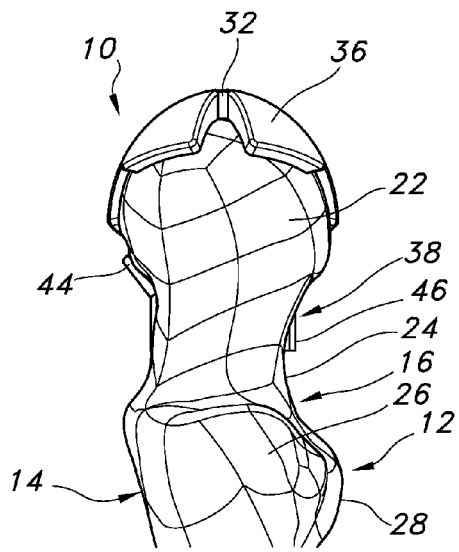
FIG. 3
FIG. 4

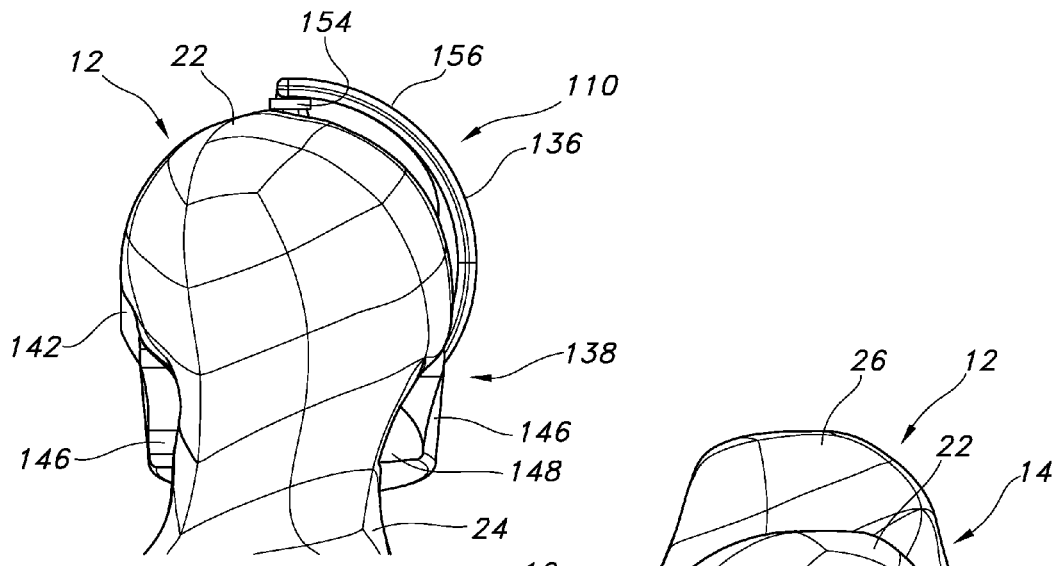
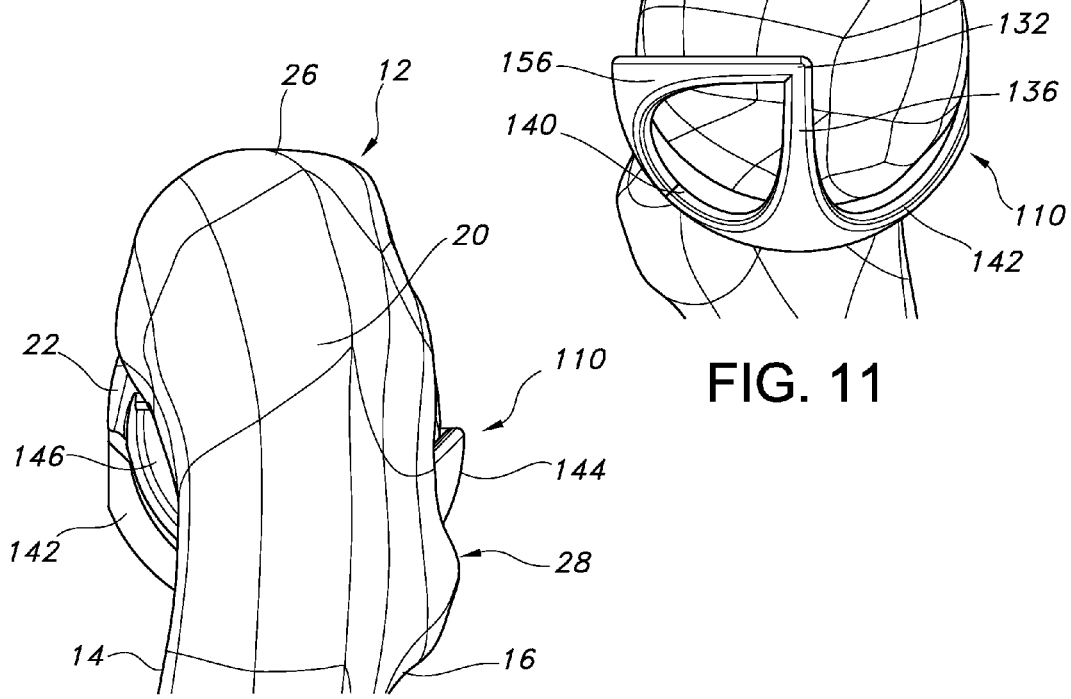
FIG. 10
FIG. 11
FIG. 12

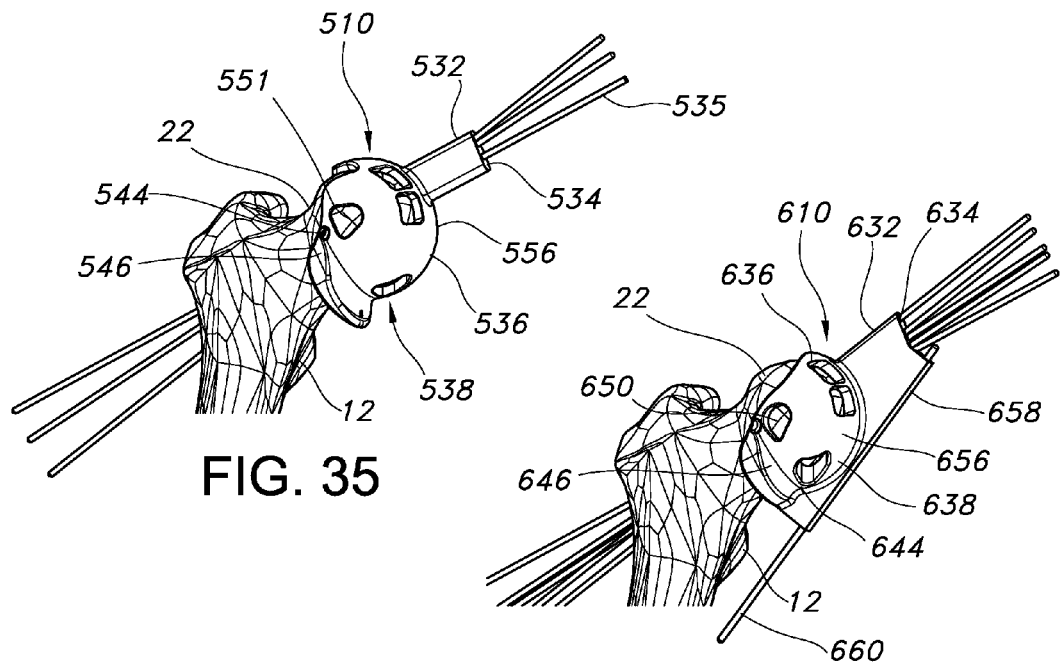
FIG. 35
FIG. 36
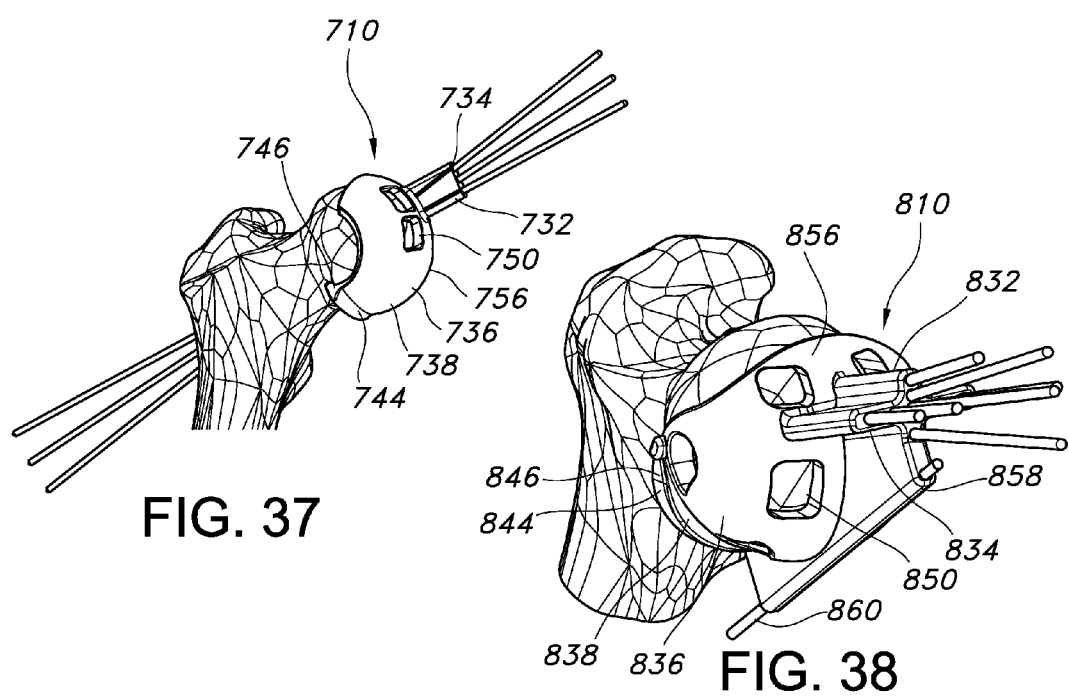
FIG. 37
FIG. 38

PATIENT SPECIFIC ALIGNMENT GUIDE FOR A PROXIMAL FEMUR

CROSS REFERENCE TO RELATED APPLICATIONS

This application claims the benefit of U.S. Provisional Application No. 61/176,455, filed May 7, 2009, titled "Patient Specific Alignment Guide for a Proximal Femur" and U.S. Provisional Application No. 61/230,064, filed Jul. 30, 2009, titled "Patient Specific Alignment Guide." Both of these Provisional Applications are expressly incorporated herein by this reference.

BACKGROUND OF THE INVENTION

1. Field of the Invention

This invention relates generally to instruments for bone modifications at a hip joint and, more particularly, for instruments designed for a patient's specific bone and cartilage.

2. Related Art

Current instrumentation is generally hard to learn, difficult to use, and time consuming. Costs may be reduced by reducing the time required to perform the surgery, as well as requiring fewer instruments. Additionally, patient specific instrumentation may also limit the invasiveness of instruments, may provide faster recovery times, and fewer complications (for example, by lowering the risk of clotting).

Work in patient specific instruments has focused primarily on the knee joint. Some art offhandedly refers to instruments and methods that may additionally be used for the hip joint. However, the art generally does not specifically focus on the important differences of the hip joint relative to the knee joint, nor focus on the specific orientations necessary at the hip for proper placement of a prosthetic device.

There remains a need in the art for a patient specific alignment guide for a proximal femur. Specifically, there is a need to provide a better and easier way of performing femoral head resurfacing procedures.

SUMMARY OF THE INVENTION

Certain embodiments of the invention constitute alignment guides for aligning instrumentation on a proximal femur. Such guides can include a neck portion configured to wrap around a portion of the neck of the femur, a head underside portion configured to abut a disto-lateral portion of the femoral head and a medial head portion with arms that are configured to overlie a medial and superior portion of the head. Portions of the guide can have an inner surface that is generally a negative of the femoral bone and/or cartilage of a specific patient that the guide overlies; such surfaces can be formed using data obtained from the specific patient by conventional imaging devices, and using computer aided design and manufacturing techniques. The neck portion can be configured to stabilize the guide rotationally by abutting and generating a first gripping force on the neck. The femoral head portions can be configured to grip the head portion of the femur and can support or include a bore guide that is configured to guide an instrument to the femur in a specified spatial location and orientation along a given axis relative to the femur. Such guides can be structured in size and shape to present minimal obstruction when being used in surgery, so that they are suitable for minimally invasive surgery such as, for instance, anterior approach hip resurfacing surgery. Their size and shape also can allow them to be easily introduced to and positioned on the patient's femur, such as from a direction distal to the femoral head. Other embodiments of the invention include methods of making and methods of installing such guides.

Accordingly, there is provided an alignment guide configured to conform to portions of a femoral neck and a femoral head of a femur of a specific patient, the guide comprising: a central member that includes at least one bore guide, the at least one bore guide oriented and configured to guide formation of a bore in the femoral head of the specific patient; a plurality of arms extending from the central member, each arm having an inner surface, at least a portion of the inner surface of each arm configured in shape to contact at least one portion of the femoral head of the specific patient; at least one head underside member connected to at least one of the arms, the at least one head underside member including an inner surface; at least one neck member connected to the at least one head underside member, the at least one neck member including an inner surface; at least a portion of at least one of the at least one head underside member inner surface and the at least one neck member inner surface configured in shape to contact at least one portion of the femur of the specific patient; wherein the portions of the inner surfaces of the arms, the at least one head underside member and the at least one neck member that are configured in shape to contact at least one portion of the femoral head and femoral neck of the patient are configured in shape using data obtained from the specific patient regarding the shape of the specific patient's femur; and wherein the plurality of arms, the at least one head underside member and the at least one neck member are configured to cause the alignment guide to grip the specific patient's femoral head during formation of the bore in the specific patient's femoral head, and to be removably retained in place on the specific patient's femoral head in order to orient the at least one bore guide to guide formation of the bore in the specific patient's femoral head.

There is also provided an alignment guide configured to conform to portions of a femoral neck and a femoral head of a femur of a specific patient, the guide comprising: a central member that includes at least one bore guide, the at least one bore guide oriented and configured to guide formation of a bore in the femoral head of the specific patient; at least two arms extending from the central member, each arm having an inner surface, at least a portion of the inner surface of each arm configured in shape to contact portions of the specific patient's femur, wherein a first of the arms is configured to extend distally from the central member when the guide is installed on the specific patient's femur, and a second of the arms is configured to extend from the central member in a direction different than the direction in which the first arm extends; at least one head underside member connected to at least one of the arms, the at least one head underside member including an inner surface; at least one neck member connected to the at least one head underside member, the at least one neck member including an inner surface; at least one of the at least one head member inner surface and the at least one neck member inner surface including a portion that is configured in shape to contact portions of the specific patient's femur; a slit formed in the central member and the bore guide, the slit configured to permit the guide to be withdrawn from a structure extending from the patient's femoral head; wherein the portions of the inner surfaces of the arms, the at least one head underside member and the at least one neck member that are configured in shape to contact portions of the femoral head and femoral neck of the specific patient are configured using data obtained from the specific patient regarding the shape of the specific patient's femur; wherein all parts of the alignment guide are configured to be sufficiently small and nonobtrusive relative to the specific patient's anatomy so as to permit the guide to be usable in anterior approach hip resurfacing surgery on the specific patient; and wherein the guide is configured to grip the specific patient's femoral head in removable fashion when placed on the specific patient's femoral head in order to allow orientation of the at least one bore guide for formation of a bore in the specific patient's femoral head.

There is also provided a method for making an alignment guide configured to conform to portions of a femoral neck and a femoral head of a femur of a specific patient, comprising: receiving data obtained from the specific patient regarding shape of the specific patient's femur; and preparing, using the data, the alignment guide, including: preparing a central member that includes at least one bore guide, including orienting and configuring the at least one bore guide to guide formation of a bore in the femoral head of the specific patient; preparing at least two arms extending from the central member, including preparing on each arm an inner surface, including automatically configuring, using the data, at least a portion of the inner surface of each arm to conform in shape to contact portions of the specific patient's femur, and including configuring a first of the at least two arms to extend distally from the central member when the guide is installed on the specific patient's femur, and a second of the at least two arms to extend from the central member in a direction different from the direction in which the first arm extends; preparing at least one head underside member connected to at least one of the arms, including preparing on the at least one head underside member an inner surface; preparing at least one neck member connected to the at least one head underside member, including preparing on the at least one neck member an inner surface; automatically configuring, using the data, at least a portion of at least one of the at least one head underside member inner surface and the at least one neck member inner surface to conform in shape to contact portions of the specific patient's femur; and wherein such preparation of the alignment guide configures all parts of the guide to be sufficiently small and nonobtrusive relative to the specific patient's anatomy so as to permit the guide to be usable in anterior approach hip resurfacing surgery on the specific patient; and wherein such preparation of the alignment guide configures the alignment guide to grip the specific patient's femoral head in removable fashion when placed on the specific patient's femoral head in order to allow orientation of the at least one bore guide for formation of a bore in the specific patient's femoral head.

There is also provided a method of installing an alignment guide configured to conform to portions of a femoral neck and a femoral head of a femur of a specific patient; including: receiving an alignment guide that comprises: a central member that includes at least one bore guide, the at least one bore guide oriented and configured to guide formation of a bore in the femoral head of the specific patient; a plurality of arms extending from the central member, each arm having an inner surface, at least a portion of the inner surface of each arm configured in shape to contact at least one portion of the femoral head of the specific patient; at least one head underside member connected to at least one of the arms, the at least one head underside member including an inner surface; at least one neck member connected to the at least one head underside member, the at least one neck member including an inner surface; at least a portion of at least one of the at least one head underside member inner surface and the at least one neck member inner surface configured in shape to contact at least one portion of the femur of the specific patient; wherein the portions of the inner surfaces of the arms, the at least one head underside member and the at least one neck member that are configured in shape to contact at least one portion of the femoral head and femoral neck of the patient are configured in shape using data obtained from the specific patient regarding the shape of the specific patient's femur; and wherein the plurality of arms, the at least one head underside member and the at least one neck member are configured to cause the alignment guide to grip the specific patient's femoral head during formation of the bore in the specific patient's femoral head, and to be removably retained in place on the specific patient's femoral head in order to orient the at least one bore guide to guide formation of the bore in the specific patient's femoral head; creating an incision in the specific patient and accessing the specific patient's femoral head; installing the alignment guide on the specific patient's femur; preparing a bore in the specific patient's femoral head using the alignment guide; resecting the specific patient's femur using the bore; installing an implant on the resected femur; and completing the surgery.

According to some embodiments, the alignment guide can comprise a curved sleeve cutter guide connected to at least one of the arms, the sleeve cutter guide configured to indicate a potential location of a surface formed by a sleeve cutter. An alignment guide according to claim 1 configured to snap on to the femur of the specific patient.

According to some embodiments, the alignment guide can comprise indicia located on an outer surface of the guide, the indicia oriented and configured to indicate alignment of the guide relative to varus/valgus angulation or version angulation.

According to some embodiments, the alignment guide can comprise a slit formed in the central member and the bore guide, the slit configured to permit the guide to be withdrawn from a structure extending from the femoral head of the specific patient.

According to some embodiments, the alignment guide can comprise a boss formed on the outer surface of the guide, the boss including structure adapted to receive a stylus for aid in alignment of the guide relative to the femoral head.

According to some embodiments, the alignment guide can comprise two head underside members, the head underside members connected to at least one of the arms and to at least one of the neck members to define a window.

According to some embodiments, the alignment guide can comprise a finger extending from the central member, the finger including an inner surface, portions of the inner surface of the finger configured in shape to conform to portions of the femoral head of the specific patient.

According to some embodiments, the alignment guide can comprise a finger bifurcated and configured to permit the guide to be withdrawn from a structure extending from the femoral head of the specific patient.

According to some embodiments, the alignment guide can comprise a guide wherein the central member, arms, at least one head underside member, and neck member are configured in shape to feature minimal size sufficient to snap on to the femoral head and to grip the femoral head while conforming to the femoral head, whereby the alignment guide is configured to be installed and withdrawn in anterior approach hip surgery on the specific patient.

According to some embodiments, the alignment guide can comprise a guide wherein at least one arm is configured to extend distally from the central member when the guide is installed on the femur of the specific patient, and another arm is configured to extend anteriorly or posteriorly from the central member when the guide is installed on the femur of the specific patient.

According to some embodiments, the alignment guide can comprise a guide wherein substantially all of the inner surfaces of the arms, the at least one head underside member and the at least one neck member are configured in shape to conform to a portion of the femur of the specific patient.

According to some embodiments, the alignment guide can comprise an alignment structure connected to the alignment guide, the alignment structure including a plane or axis that is substantially coplanar to a longitudinal axis of at least one bore guide.

According to some embodiments, the alignment guide can comprise a plurality of bore guides, the bore guides configured and oriented to allow adjustment of angulation of the bore formed in the specific patient's femoral head in at least one of varus/valgus and version angulation.

According to some embodiments, the alignment guide can comprise a plurality of bore guides, the bore guides configured and oriented to allow adjustment of angulation of the bore formed in the specific patient's femoral head in at least one of varus/valgus and version angulation, wherein the bore guides are formed in the central member, and the central member is generally planar in shape.

According to some embodiments, the alignment guide can comprise a plurality of bore guides, the bore guides configured and oriented to allow adjustment of angulation of the bore formed in the specific patient's femoral head in at least one of varus/valgus and version angulation, wherein the bore guides are formed in the central member, and the central member is generally cruciform in shape.

Advantages of certain embodiments of the invention accordingly include alignment guides (and methods for making and using them) for the femur that:
- allow accurate positioning of a bore in the femoral head and neck, in either or both location and angular orientation, for hip resurfacing or other hip surgery;
- can feature inner surfaces that are prepared in a patient specific manner, according to data obtained from a specific patient, for positioning and orienting a bore in the femoral head in either or both location and angular orientation, for hip resurfacing or other surgery;
- can be prepared using computer aided design and/or computer aided manufacturing techniques and patient specific data, in addition to, if desired, input or data from the surgeon;
- can be made sufficiently small and nonobtrusive to allow for use in minimally invasive surgery, including anterior approach hip surgery, but yet can retain their position on the femoral head and neck once placed in position for accurate location, orientation and angulation of a bore in the femoral head; and/or
- can be introduced to the femoral head from a distal direction relative to the femoral head.

Further features and advantages of at least some of the embodiments of the invention, as well as the structure and operation of various embodiments of the invention, are described in detail below with reference to the accompanying drawings.

BRIEF DESCRIPTION OF THE DRAWINGS

The accompanying drawings, which are incorporated in and form a part of the specification, illustrate embodiments of the invention and together with the description, serve to explain the principles of such embodiments. In the drawings:

FIGS. 1 through 5 are views of a patient specific alignment guide attached to a femur according to an embodiment of the invention;

FIGS. 6 through 12 are views of a patient specific alignment guide attached to a femur according to an alternate embodiment of the invention;

FIGS. 35-38 are views of additional patient specific alignment guides according to alternate embodiments of the invention.

DETAILED DESCRIPTION OF VARIOUS EMBODIMENTS

Figure 5:
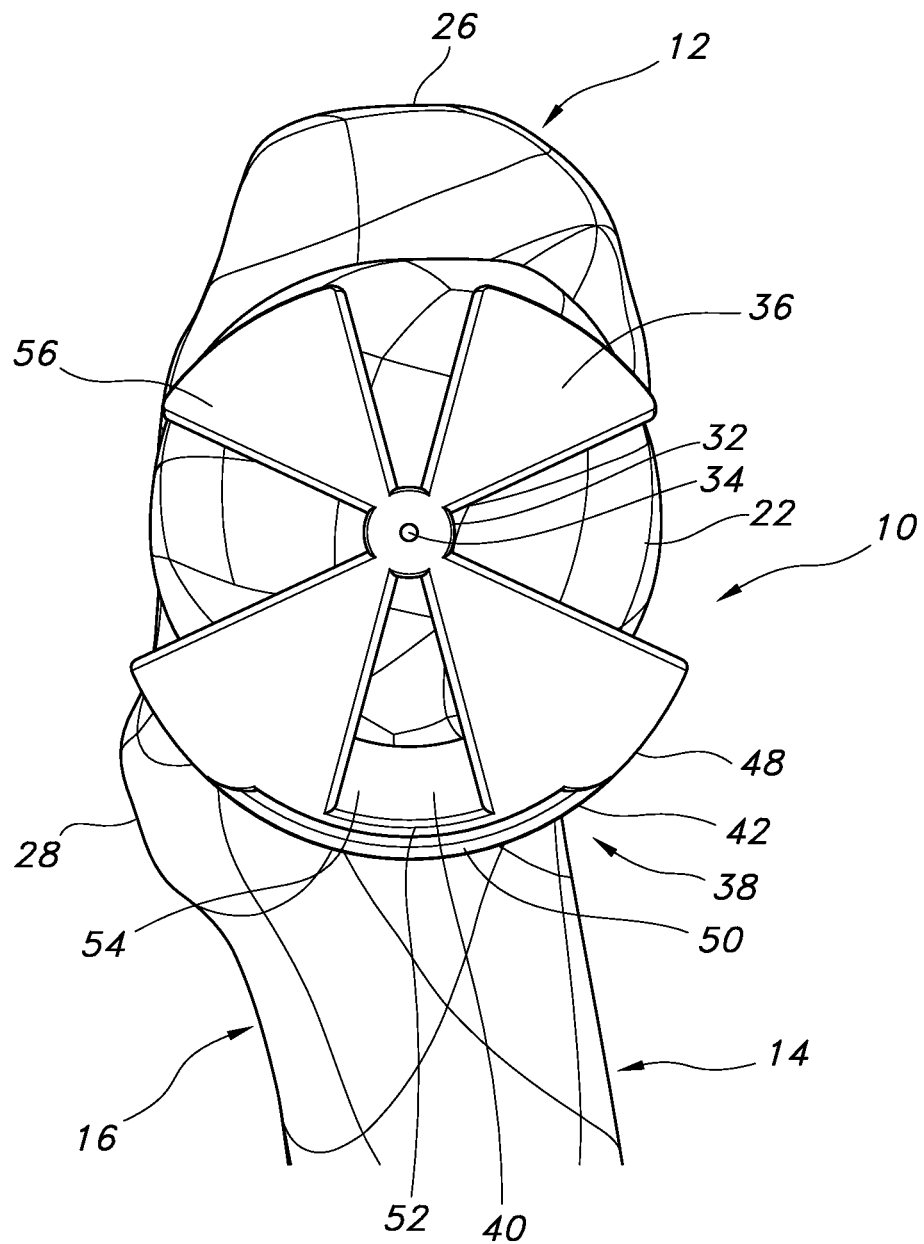

FIGS. 1-5 illustrate views of a patient specific alignment guide 10 attached to a femur 12 (in this case a left femur) according to an embodiment of the invention. FIG. 1 is a posterior view of the guide and the femur. FIGS. 2-5 are a distal view, anterior view, proximal view and medial view, respectively, of the guide 10 and femur 12.

The alignment guides of all the embodiments are generally meant to locate an axis into the head and neck of the femur 12 in order to position the axis and form a bore that can be used with subsequent instrumentation for a hip surgery, for example a hip resurfacing surgery such as the procedure for preparing anatomy for acceptance of a Birmingham Hip Resurfacing® (BHR) implant by Smith & Nephew, Inc. This axis, because the neck tapers down, must be accurately located in order to align the implant properly. Moreover, proper placement on the head of the femur must be found in order to avoid notching portions of the femoral neck during the resurfacing procedure. Thus, at least some of the position of the axis, both anterior/posterior and proximal/distal, as well as at least some of angulation in varus/valgus and in version, are important and can be controlled by alignment guides of embodiments of the invention.

Briefly, femur 12 includes an anterior side 14, a posterior side 16, a medial side 18 and a lateral side 20. Femoral head 22 protrudes generally medially from neck 24, which in turn protrudes generally medially from femoral shaft 30 of femur 12. Greater trochanter 26 and lesser trochanter 28 which can be seen most clearly in a posterior view such as FIG. 1, are prominent landmarks of the proximal femur.

The alignment guide 10 of FIGS. 1-5 includes a central member 32 which includes a bore guide 34. The central member 32 is connected to a plurality of arms 36. In the embodiment shown in FIGS. 1-5, two such arms 36 connect to a cradle 38 that is formed of a first web member 40 and second web member 42, a head underside member 44, and a neck member 46. Shoulders 48 reduce material to tailor flexibility, and can form a portion of cradle 38 in the area where second web member 42 transitions to head underside member 44. In the embodiment shown in FIGS. 1-5, a window 50, which may be used for navigating guide 10 or as otherwise desired, is bordered by first web member 40, second web member 42 and structure that connects arms 36 to those members.

The alignment guide of FIGS. 1-5 is configured to fit portions of the head 22 and neck 24 of femur 12. In this embodiment, both head 22 and neck 24 contact femur 12 sufficiently to obtain proper fixation of the guide 10 on the femoral head 22 and neck 24, in at least sufficient three point fixation. The arms 36 of guide 10 extend over the femoral head 22 and are configured to snap on to the head 22 for helping to locate the placement of the guide 10 on femur 12 in a single predetermined orientation relative to the femur 12. The central member 32 includes sufficient structure to allow bore guide 34, which may be a bore, opening, channel, slot, track, protuberance, or any other desired structure, to guide an instrument that in turn guides a drill, to guide a drill, or otherwise to guide, directly or indirectly, formation of a properly located and oriented bore in femoral head 22. The thickness of other portions of the guide 10, such as arms 36, and various parts of the cradle 38, may be configured as desired to allow flexibility for placement of the guide 10 on femur 12 while sufficiently structurally rigid to maintain the guide 10 on femur 12 as an instrument or drill is being guided in bore guide 34 of central member 32 of guide 10 to form the axial bore in the femoral head 22.

The window 50 helps a surgeon have better visualization of the femoral head 22 as the guide 10 is being used and ensures the guide 10 is properly seated on the femoral head 22. The arms 36 can be adjusted in position on femoral head 22 to account for proper varus/valgus and version angle alignment. Such movement of the arms 36 results in shifting the central member 32 and consequently the bore guide 34 into proper varus/valgus and/or version alignment. The cradle structure 38 including head underside member 44 and neck member 46 can also contact the femur 12 in the course of such positioning. Thus, the angle of the axis and bore defined by bore guide 34 is controlled by such positioning of the arms 36 and portions of the cradle 38.

The guide 10 is configured to contact the femur 12 around the head 22 and neck 24 so that a gripping force is exerted through at least portions of the inner surfaces 54 of arms 36 and portions of the cradle 38 onto the femur. These portions of inner surfaces 54 are configured to conform to and/or contact the surface of the bone while the gripping forces are generated through elastic deformation of the material the guide 10 as the guide 10 is placed in contact with the femur 12. Such conforming portions of inner surfaces 54 that are designed actually to contact femur 12 can be minimized to minimize effect on soft tissue around the proximal femur, they can form substantially all of such inner surfaces 54 on any or all of arms 36 and cradle 38, or they can range anywhere between these extremes. For instance, one or more point contacts, line contacts (arched, arciform, bent, bowed, curved, curvilinear, or straight), surface area contacts and combinations thereof may be formed on any one individual inner surfaces 54.

In order for the gripping forces to hold the guide 10 to the head 22, the forces must generally act upon the femur 12 toward a point inside the head 22 of the femur 12 or be counteracted by an opposing force generated through another inner surface 54 of the guide 10. Thus, the total resultant force on the guide 10 should be relatively small, once all the opposing forces are reduced to cause the guide 10 to grip the head 22 properly.

In order for opposing forces to exist on the femur 12 and guide 10, the guide 10 should preferably extend about to or greater than hemispherically around the head 22 of the femur 12. In the embodiment shown in FIGS. 1-5, the guide 10 extends generally from a proximo-medial point on the femoral head 22 that is anterior/posteriorly neutral, to a disto-lateral, anteriorly/posteriorly neutral point.

At least portions of the inner surfaces 54 of arms 36, cradle 38, first web member 40, second web member 42, head underside member 44, and neck member 46 may be determined and formed using x-ray, computerized tomography (CT) scans, magnetic resonance (MRI) scans, and/or high definition ultrasound imaging, but may also be determined and formed using other bone scans that may visualize the bone and cartilage of the joint. The surfaces 54 may be slightly undersized in order to create the interference that causes the gripping forces. The thickness and width of the guide 10 around the head affects the elasticity of the guide 10 and thus affects how much undersizing can be achieved as a tradeoff to the elasticity. The x-ray and/or MRI data may be taken by known means. As an example, the following protocols may be used. Different MR protocols may be executed on different patients. To minimize scan time, a fast spin echo imaging technique may be used for any protocol, essentially producing a proton density (PD) weighted image. One protocol may use the spoiled gradient echo technique with a low repetition time (TR) and low echo time (TE) and a flip angle of 30 degrees combined with a fat saturation technique. A second protocol and third protocol may use a high TR and a low TE combined with a fat saturation technique. The only difference between the second protocol and third protocol is that the second protocol has lower TE than the third protocol, which in turn offers more T1 and less PD properties. The increased T1 relaxation time may help to increase the image contrast within the different tissues in the MR image. Bone models of the femur 12 may be extracted from the MR images and appropriate anatomic reference landmarks may be identified. Full leg x-rays may be used to determine the mechanical axis alignment and/or total version. The guide 10 particularly including inner surfaces 54, can then be designed and prepared through computer-aided design (CAD) modeling such that the structure of guide 10 conforms to bone models for proper seating on femoral head 22 and neck 24 so that bore guide 34 may be properly located in position and angulation using guide 10. The CAD and other automated techniques according to certain embodiments of the invention can be configured to accommodate input or definition from the surgeon, if desired, on matters such as various dimensions of various parts of guide 10, intended bore location, angulation and path, and/or shape, dimensions or other characteristics of resections or implants to be performed or used in connection with guide 10. Guide 10, or at least portions of inner surfaces 54 of guide 10, may be made from medical grade nylon 12 or other desirable material using, for example, laser techniques such as the EOSintP or any other desired computer aided manufacturing system. Since the inner surfaces 54 are based on the patient's data set, clean data (properly differentiating between bone and cartilage and soft tissue) should be used to ensure the fit and functionality of guide 10.

FIG. 5 shows indicia 52 which can be scored, marked or otherwise formed on outer surfaces 56 of guide 10 to help the surgeon reference varus/valgus and/or version angulation and other navigational or directional planes or directions of interest. In some embodiments, indicia 52 may be placed on one or more arms 36.

Figure 6:
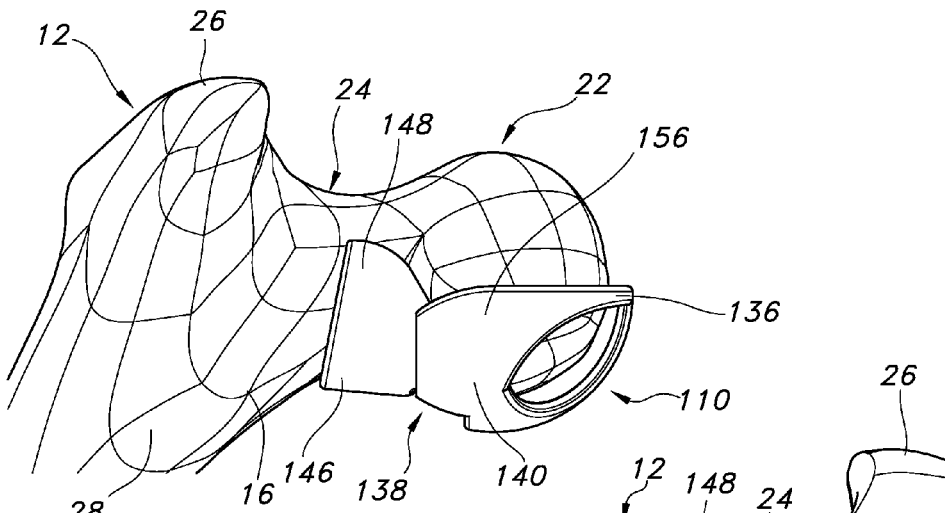
Figure 9:
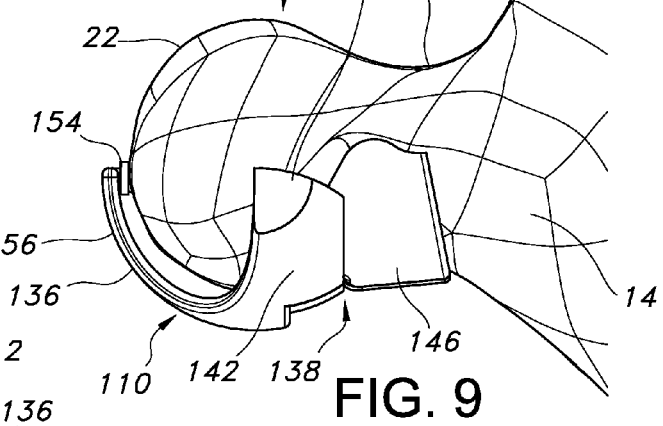
Figure 7:
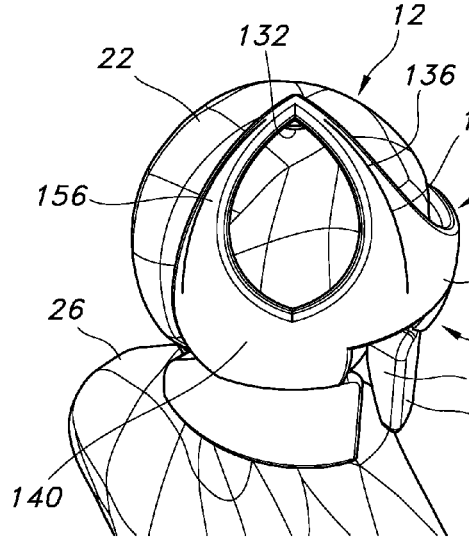
Figure 8:
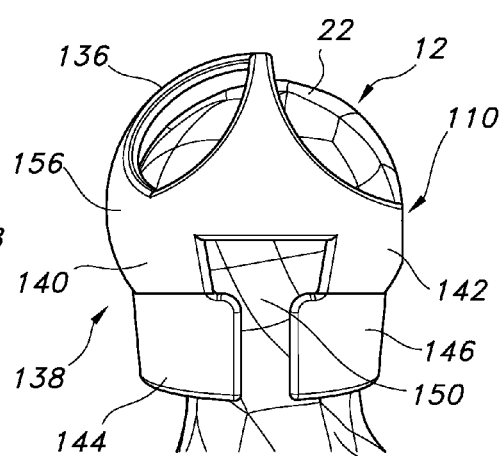

FIGS. 6-12 illustrate views of a patient-specific alignment guide 10 attached to a femur 12 according to an alternate embodiment of the invention. FIG. 6 is a posterior view of the guide 110 and the femur 12. FIG. 7 is an orthogonal view from a distal-posterior viewpoint. FIGS. 8-12 are a distal view, anterior view, proximal view, medial view and lateral view, respectively, of the guide 110 and femur 12.

The alternate embodiment of FIGS. 6-12 is similar in some ways to the previous embodiment in that it extends partially around the femoral head 22 and grips the femur 12 to hold the guide 10 in place. However, this embodiment may be used when the cartilage may not be fully visualized (for example, with a CT scan). In such an embodiment, contact along the cartilaginous surfaces is lessened to avoid improper alignment or undesirable impingement. Thus, as can be seen in the figures, not all of the inner surfaces 154 of the guide 110 are shaped in a patient-specific manner to conform to bone, as is the case with the previous embodiment, but rather only portions of such inner surfaces 54 as are designed to contact portions of the anatomy for proper placement of guide 110.

Guide 110 includes a central member 132 that connects to two arms 134, each of which connect, respectively, to a first head underside member 140 and second head underside member 142 that form portion of cradle 138. The underside members 140, 142 in turn connect to first neck member 144 and second neck member 146, respectively, to form a split neck member structure. A shoulder 148 can extend from either or both neck members 144, 146 for additional flexibility. The split neck structure created by first neck member 144 and second neck member 146 also provides a window 150 for helping in navigating the guide 110. Indicia 152 can be formed on outer surfaces 156 of arms 136 for additional navigation information. In this case, a first indicia 152 is on a first of the arms 136 for help in navigating in varus/valgus and a second indicia 152 is on another of the arms 136 for assistance in navigating in version.

To minimize tissue removal from the femoral neck 24, the guide 110 may feature reduced area along the femoral neck 24. The wrap-around of the guide 110 around the femoral neck 24 may stabilize the guide 110 rotationally and allow guide 110 to be placed carefully and cautiously along the neck to avoid the artery running along the superior-posterior femoral neck 24. The two femoral neck members 144, 146 form the window 150 which in addition to giving the surgeon more information can also help minimize contact which may be unnecessary in this region since inferior-superior axis support is provided by the contact of head underside members 142, 144 under the femoral head 22. Thus, window 150 can also for flexion of the guide 110 in abutting the femoral neck 24. The two arms 136 running along but largely clear of the femoral head 22 provide additional stability for the surgeon during drilling and will accommodate a pivot guide or bore guide 134 (not shown). The orientation of the arms 36, which are generally orthogonal to each other, also help serve to check varus/valgus and version alignment indicated by indicia 152. The structure of guide 110 is configured to be as close to the femur 12 as possible to avoid interference with tissue, and to give the surgeon space to view the intended drill path. Such minimal structure allows, for example, use of guide 110, as is the case with other guides according to some embodiments of the invention, in minimally invasive surgery and in hip surgeries where an anterior approach is used. Guide thickness maintains a rigid bore guide 134 while keeping the instrument 110 small and as flexible as necessary.

Figure 13:
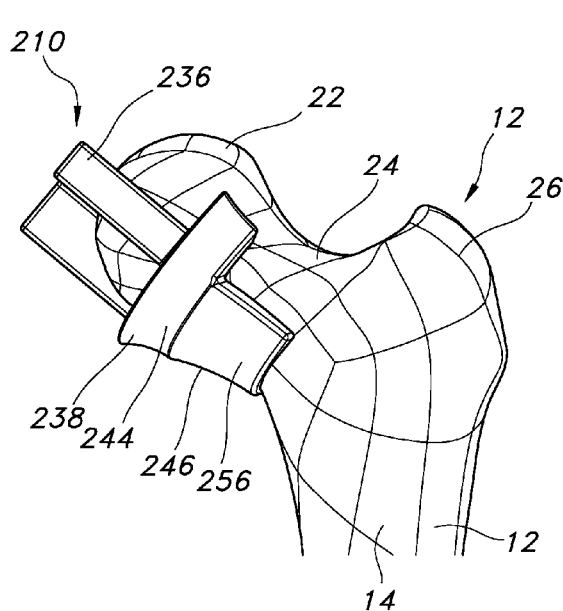
FIGS. 13 through 16 are views of a patient specific alignment guide attached to a femur according to an alternate embodiment of the invention.
Figure 14:
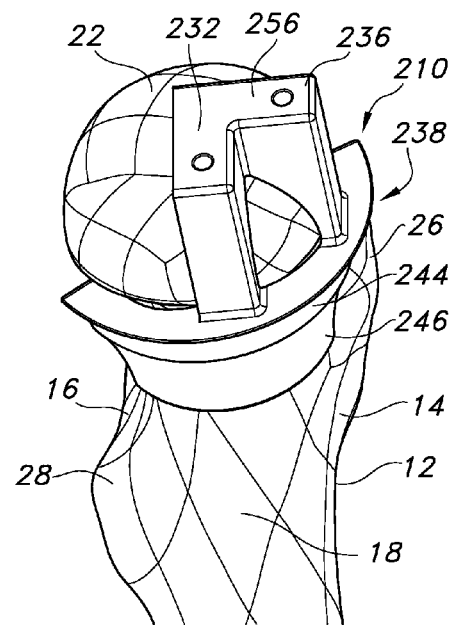
Figure 15:
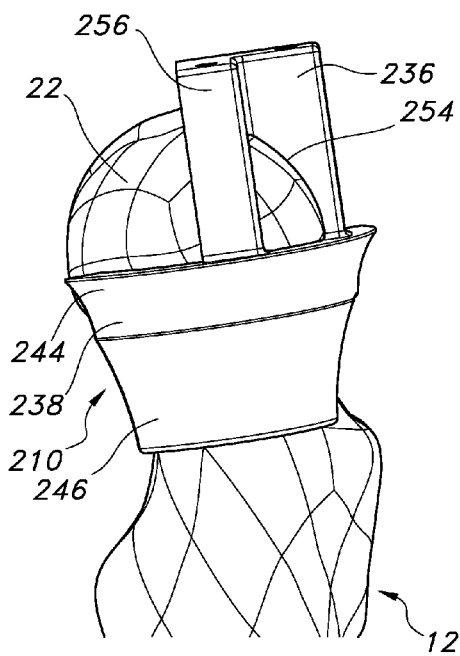
Figure 16:
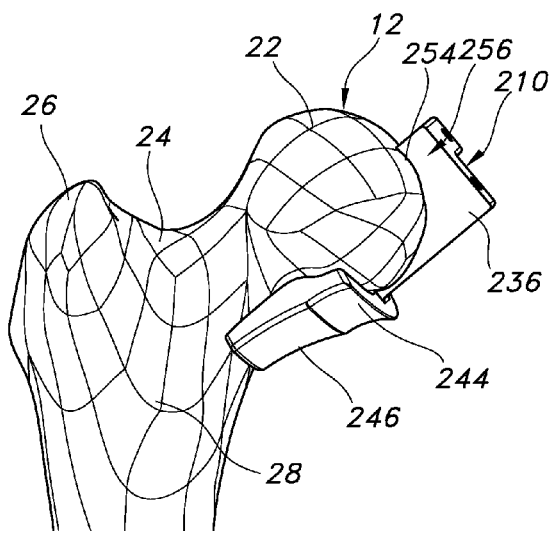

FIGS. 13-16 illustrate a patient-specific guide 210 attached to a femur 12 according to another embodiment of the invention. FIG. 13 shows an anterior view of the guide 210 and the femur 12. FIG. 14 illustrates a disto-medial orthogonal view of the guide 210 on the femur 12. FIGS. 15 and 16 illustrate a distal view and a posterior view, respectively. In this embodiment, a significant portion of the underside of the head 22 and the neck 24 is contacted by the head underside member 244 and neck member 246 of cradle 238. This fit stabilizes the guide 210 rotationally along a lower, generally hemicylindrically shaped portion. The head underside member 244 can take the form of a partial ring whose inner surface 254 (and outer surface 256 if desired) form a cone or fluted shape that extends proximally from the more generally cylindrically-shaped neck member 246. The head underside member 244 contains an additional portion that extends anteriorly around the femoral head 22 to support one of the two arms 236 of the guide 210, which are in this case orthogonally oriented relative to each other to allow the surgeon to visualize varus/valgus alignment and version alignment more easily, for additional confidence in the operating room. These arms 236, whose outer surfaces 256 can contain essentially planar surfaces that are parallel to the longitudinal axis of bore guide 34. The additional material in these arms lends rigidity to the structure of guide 210. Inner surfaces 254 or portions of them can be formed using patient data as disclosed above for patient specificity. One or more pin holes 258 may be provided on guide 210 to secure the guide 20 to one or more portions of the femur 12.

Figures 17, 18:
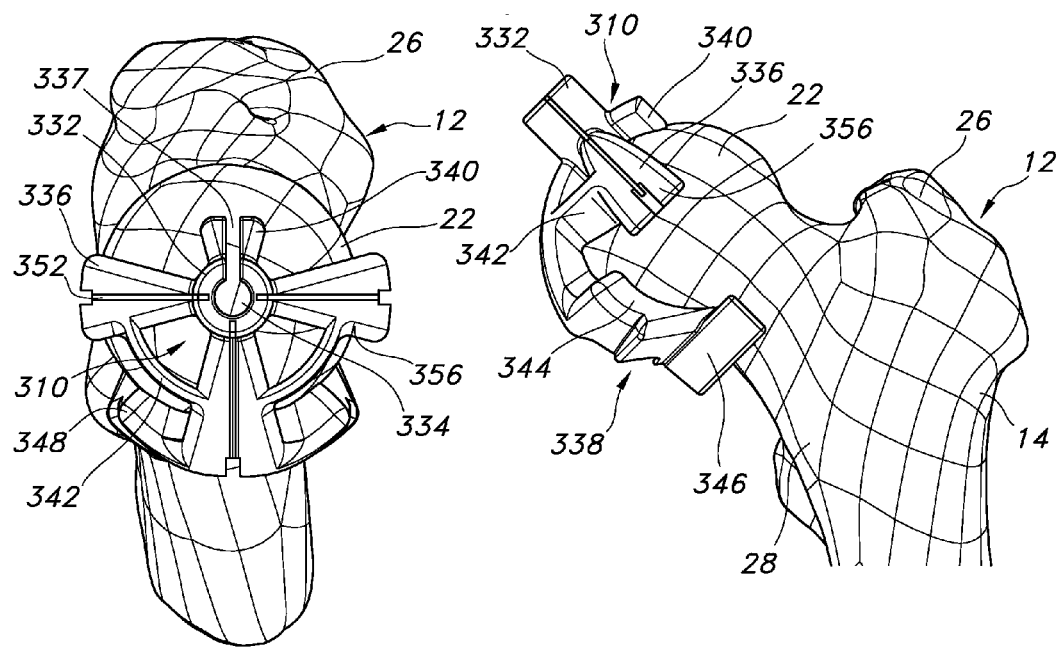
FIGS. 17 and 18 are views of a patient specific alignment guide attached to a femur according to an alternate embodiment of the invention.

FIGS. 17-20 show two additional embodiments of the invention that are generally similar to each other except for a sleeve cutter reference ring 342 that forms part of the guide 310 of the embodiment shown in FIGS. 17 and 18. The sleeve cutter reference ring 342 references, for purpose of navigation, the cylindrical surface profile that a sleeve cutter will form on the femoral head 22 for a given location and orientation of bore guide 344. Visualization allows a surgeon to see how far a sleeve cutter would extend from the center point around the edge of the femoral head 22. This allows the surgeon to gain, among other things, an understanding of whether the sleeve cutter will notch the femoral neck 24, and whether the guide 310 is otherwise aligned properly.

Figures 19, 20:
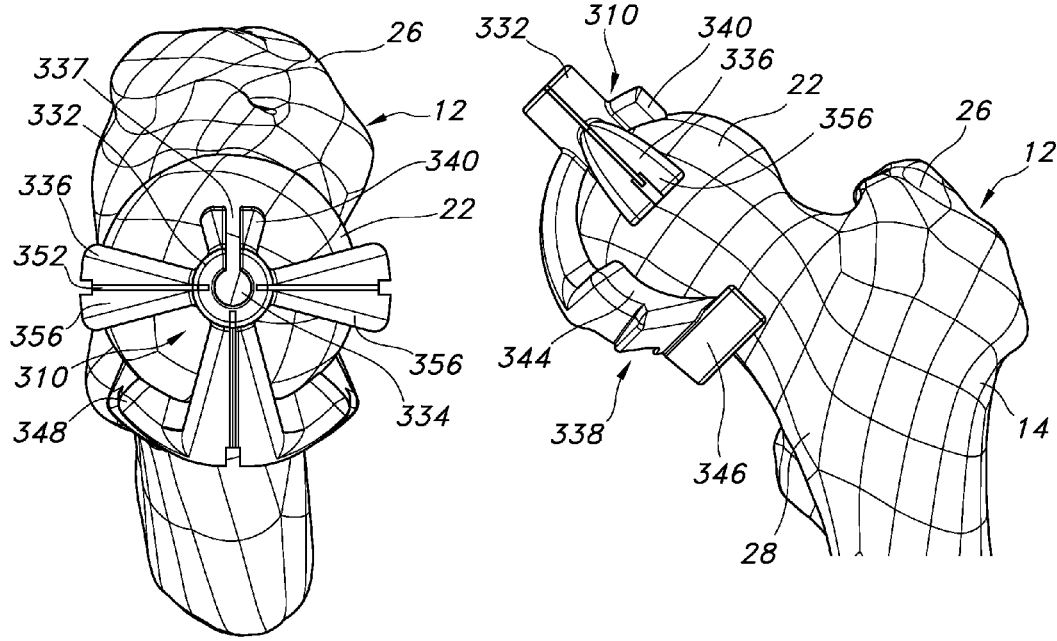
FIGS. 19 and 20 are views of a patient specific alignment guide attached to a femur according to an alternate embodiment of the invention.
Figure 21:
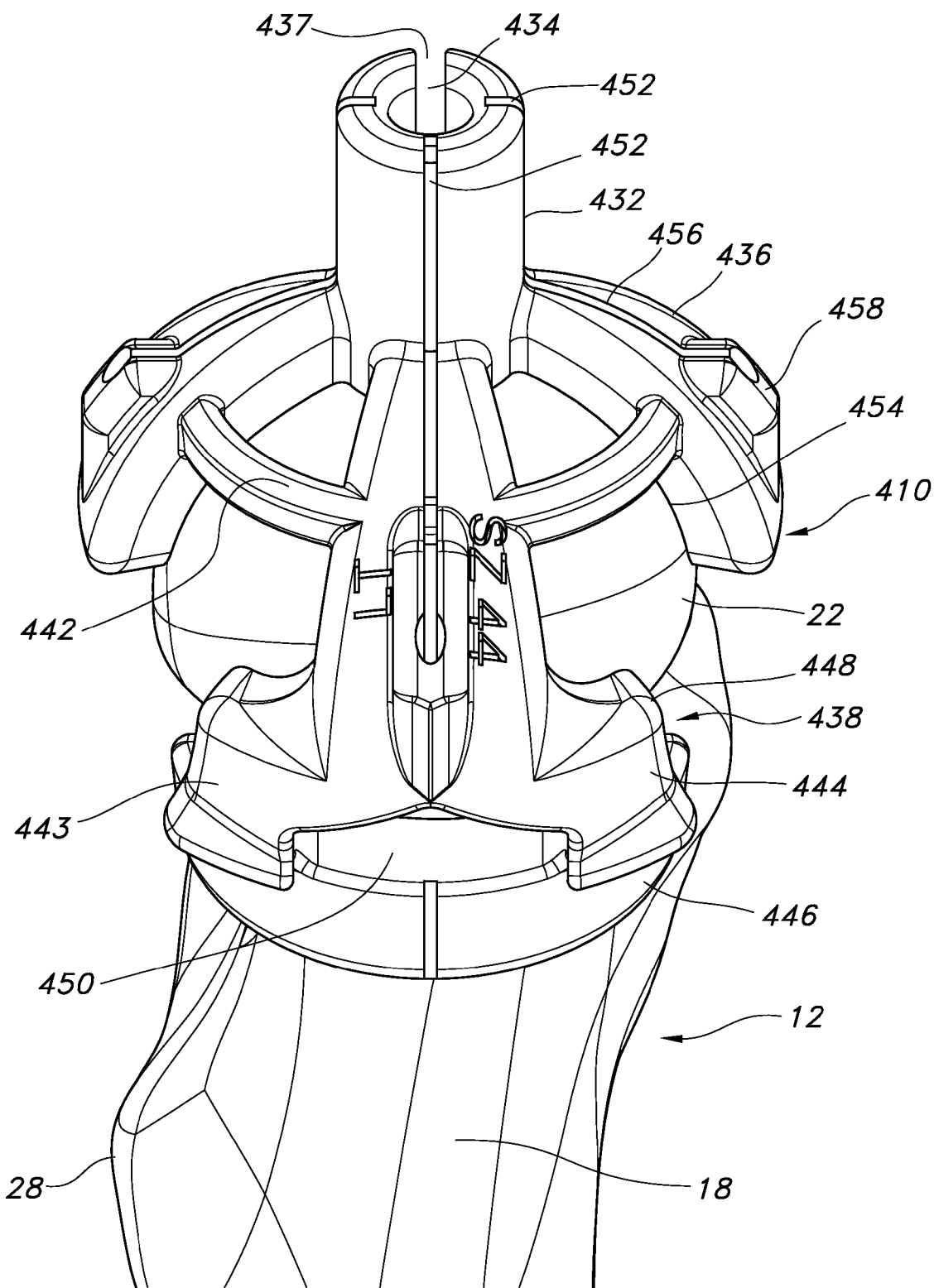
FIGS. 21 through 25 are views of a patient specific alignment guide according to an alternate embodiment of the invention.
Figure 22:
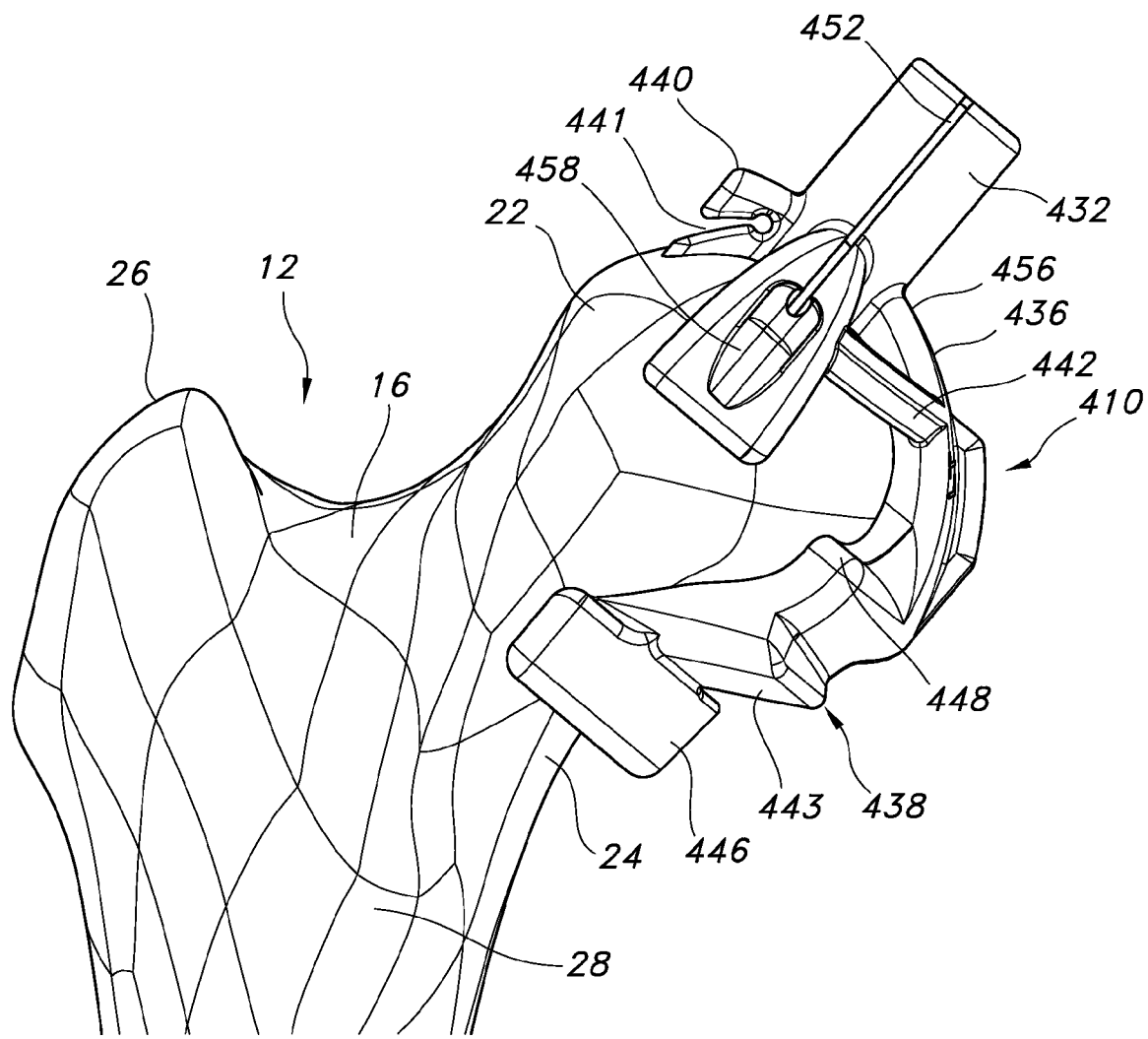
Figure 23:
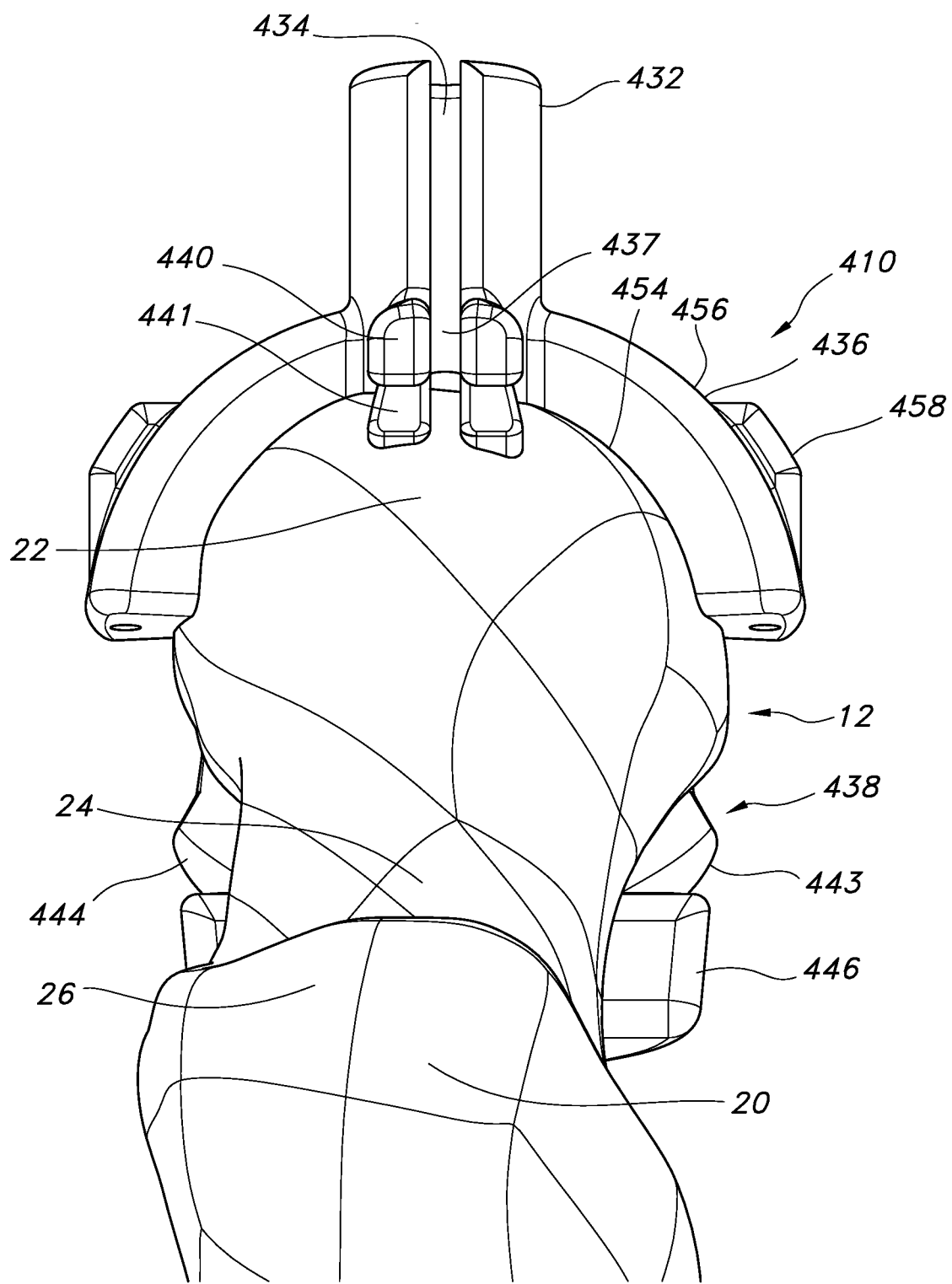
Figure 24:
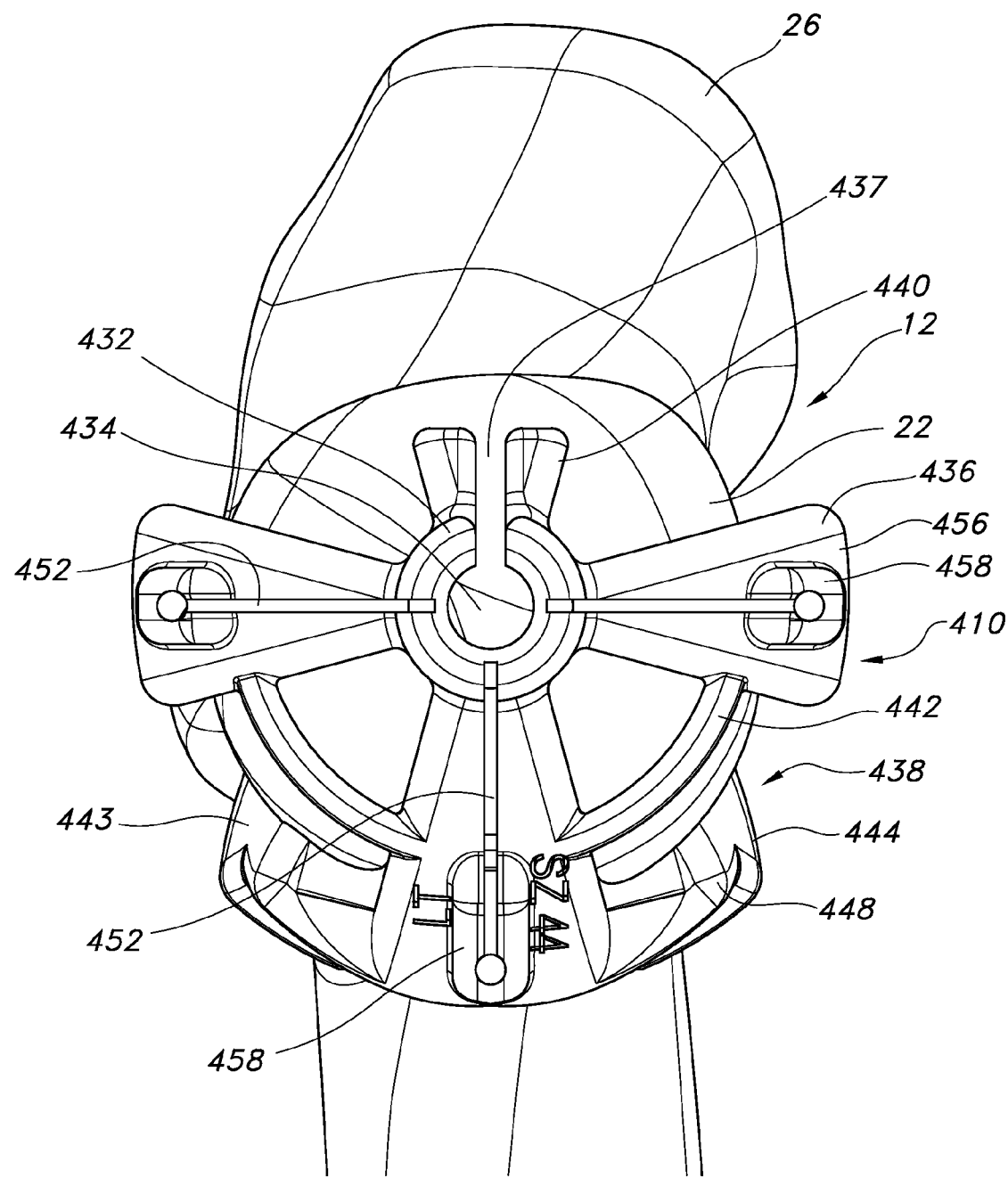
Figure 25:
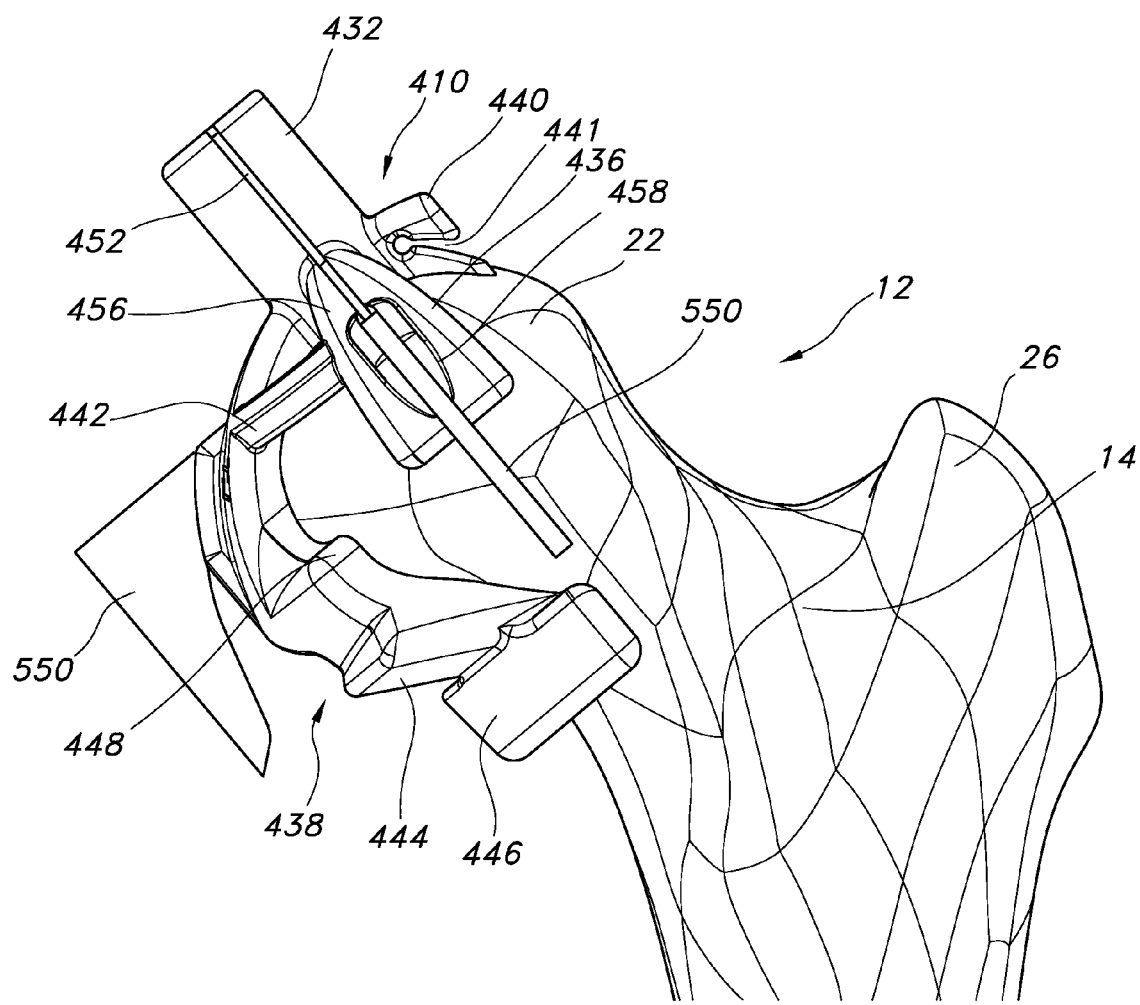

Guide 310 as shown in FIGS. 17-20 contains a central member 332 that is configured as shown most clearly in FIGS. 17 and 19 to form a split 337 in bore guide 334. A split finger 340 extends superio-laterally to take the place of one of the arms 336 and provide a predetermined degree of contact or gripping on the femoral head 22. Arms 336 extend generally in the anterior, posterior and distal directions from central member 332, when guide 310 is located on the femur 12, and a head underside member 344 connects to the arm 336 that extends in the distal direction from central member 332. The head underside member 344 connects to a neck member 346 that forms a portion of a cylinder or otherwise a generally arcuate body such as a portion of a toroid. A shoulder 348 helps tailor flexibility of the guide 310 and define outer surfaces 356 at portions of the cradle structure 338 where neck member 346 transitions to head underside member 344. Inner surfaces 354 or portions of them can be formed in a patient-specific manner using data obtained from the patient as disclosed above. Indicia 352 may take the form of printed markings, etchings, slots or the like that are located distally, anteriorly and posteriorly around the head 22 to allow for a straight edge to extend, if desired, along the axis of the femoral neck 24. Such slots accordingly help a surgeon determine that the guide of 310 is properly aligned relative to femur 12. The split central member 332 and finger 340 can allow the guide 310 to flex as it extends around the head 22 and can also allow the guide 310 to be removed or withdrawn distally, medially, transversely, or as otherwise desired from a pin or other structure (not shown) that is placed through the central member 332. The neck contact of the embodiments shown in FIGS. 17-20 can extend 180 degrees around the femoral neck 24 distally to stabilize the guide 310 in rotation while opposing forces through the arms 336 and the cradle 338 center the guide at 310 in the proper position.

FIGS. 21-25 show a guide 410 according to an alternate embodiment of the invention. Guide 410 includes a central member 432 connected to finger 440 in which the central member 432 and finger 440 feature a split 437 that divides both the bore guide 434 and the finger 440. A slot 441 may be formed in finger 437 in a plane generally orthogonal to the split 437 in order to provide additional flexion in elements of finger 440, which when divided by split 437 and slot 441 contains four such elements.

Central member 432 preferably contains a bore guide 434 which, as mentioned above, is defined in part by split 437 to allow additional flexibility for guide 410 when being installed on the femoral head and also to allow guide 410 to be removed more easily from a pin (not shown) inserted in the femoral head 22 through bore guide 434 or otherwise. Guide or jig designs that do not use such a split 437 can require axial removal via cannulation or otherwise, thereby requiring more space in the anatomy in which to remove the such a guide, as well as reducing options for placing the guide on the femoral head and for clearing some portions of the design from portions of the femoral head such as in the vicinity of the neck during extraction. However, such non-split bore guides can be used in embodiments of the invention where desired, such as in the event that structural integrity issues outweigh these axial removal issues. Arms 436 extend generally anteriorly, posteriorly and distally from the central member 432. The arm 436 that extends distally from the central member 432 connects to first-head underside member 443 and second-head underside member 444 which in turn connect to neck member 446 that is configured to extend around a portion of the femoral neck 24, preferably a distal, antero-distal, or postero-distal portion of neck 24. The first-head underside member 443 and second-head underside member 444 can contain shoulders 448 which give them additional torsional stability as well as desired flexibility, and to help extend the first head underside members 443, 444 around the periphery of the femoral head 22 underside. A window for 50 is defined by head underside members 443 and 444 and neck member 446 to allow the surgeon to gain additional information relative to navigation and placement of guide 410 and as otherwise desired.

Inner surfaces 454 of central member 432, arms 436, finger 440, head underside members 443, 444, neck member 446, and shoulder 448, or portions of them, can be formed in a patient-specific manner using data obtained from a specific patient as disclosed above. A sleeve cutter reference ring 442 is connected to arms 436 to indicate to the surgeon reference information about surfaces and profiles to be formed by a sleeve cutter oriented in accordance with the current position of the bore guide 434.

A score or other desired indicia 452 can be located on one or more arms 436 to provide reference information to the surgeon to locate and orient the guide 410 properly in varus/valgus and version. A plurality of bosses 458 can be formed on outer surfaces 456 of arms 436 and configured to receive guide wires or other stylii or indicators to allow the surgeon to gain additional information about placement of the guide 410 relative to the axis of the femoral head 22 and/or neck 24. Alternatively, while not shown, bosses 458 themselves may be provided as planar or elongated members and serve as integrally provided styli and indicators. In such instances, bosses 458 may generally protrude or extend in any direction generally coplanar with the longitudinal axis of the bore guide 434. Additional indicia 452 can include product size and other identifying information.

Various embodiments of the invention, particularly the embodiments shown in FIGS. 21-25, can allow the thickness of the central member 432, each arm 436, the finger 440, the underside members 443, 444, the neck member 446 and other structures as desired to be changed independently of one another so that some may grow and some may shrink in thickness according to patient-specific data and requirements. The idea is to optimize the thickness of various structural portions of the guide 410 within a general range in order to maintain appropriate structural rigidity, proper clamping forces, and optimal fit. Similarly, when patient data suggest that it would be appropriate to omit or add another arm 436 or other component, that option can be carried out.

Various embodiments of the invention, particularly the embodiments shown in FIGS. 21-25, can allow shape inner surfaces 454, or portions of such surfaces 454 of central member 432, each arm 436, finger 440, underside members 443, 444, neck member 446 and other structures independently of one another. For example, one arm 436 can feature a larger area of inner surface 454 that is shaped in a patient specific manner and/or to contact bone and/or cartilage, than the patient specific shaped area of another arm 436. Similarly, patient specific shaped areas can be omitted as desired from some or all arms 436, central member 432, finger 440, cradle 438, underside members 443, 444, and neck member 446. As previously mentioned, the patient specific shaped areas may be provided as any one or combinations of point contacts, line contacts, and surface area contacts to contact the femur of the specific patient.

Figure 26:
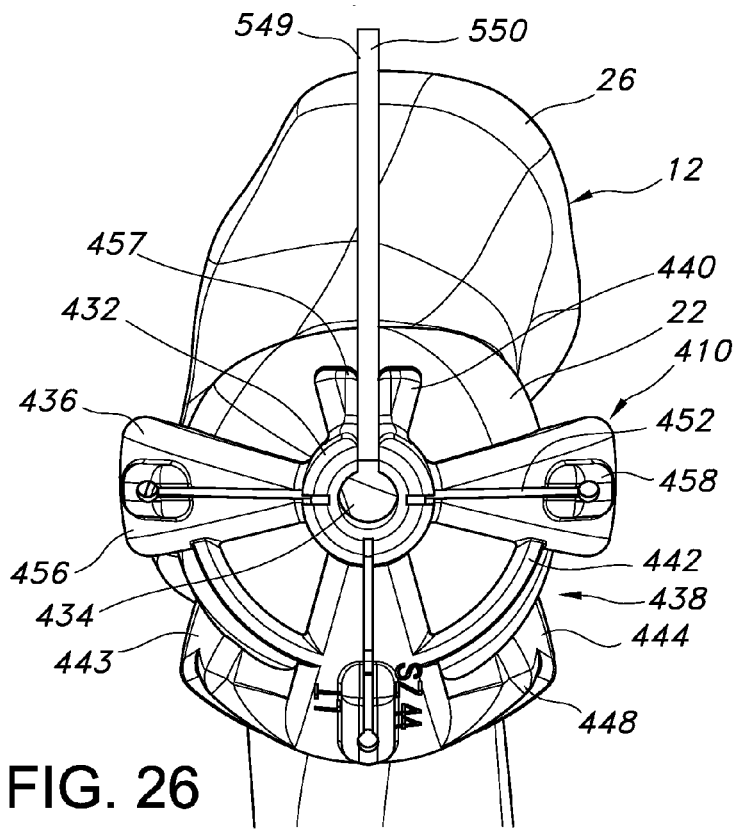
FIGS. 26-28 are views of various stylii according to various embodiments of the invention.
Figure 27A:
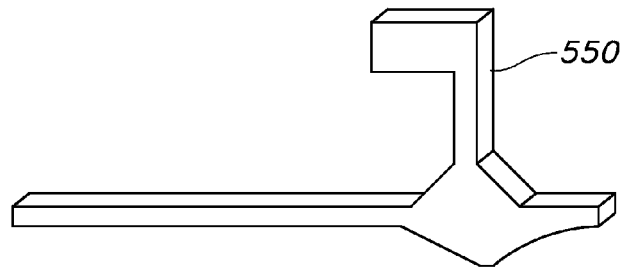
Figure 27B:
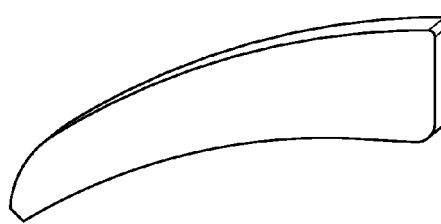
Figure 28:
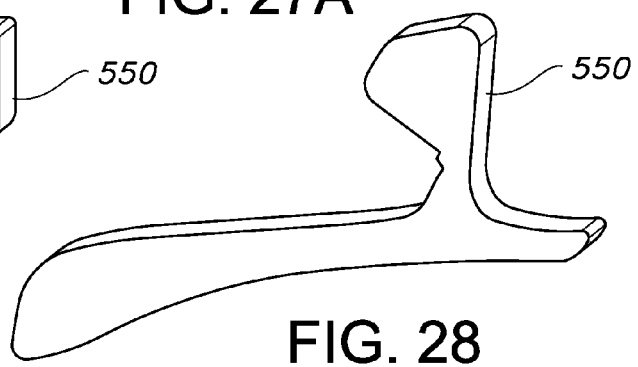
Figure 29:
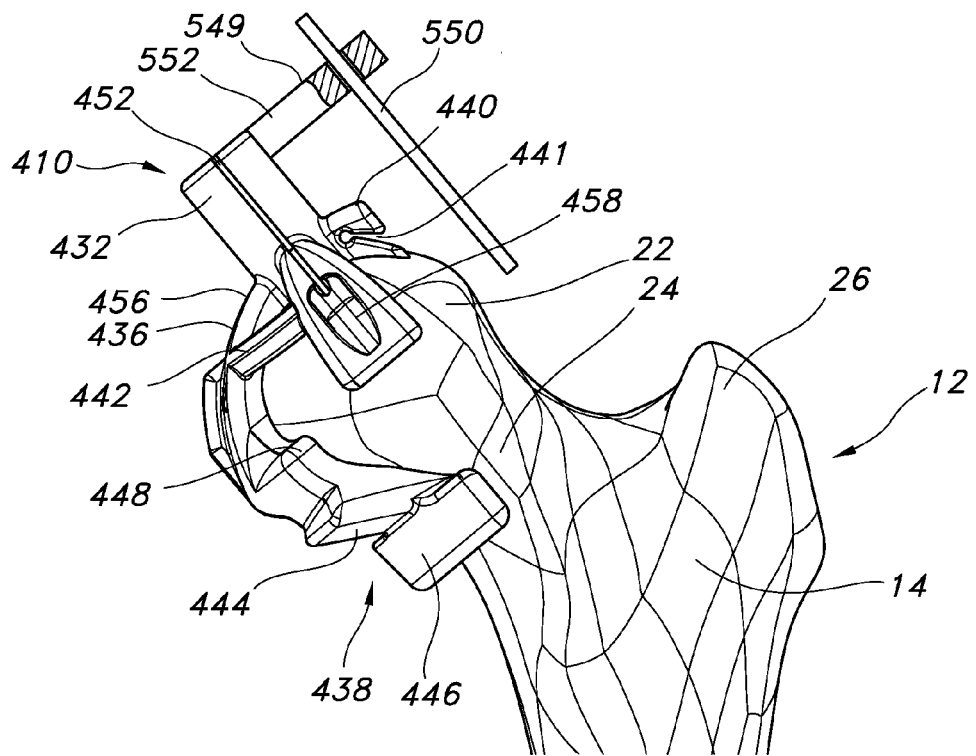
FIGS. 29 and 30 are views of alignment indicators according to certain embodiments of the invention.
Figure 30:
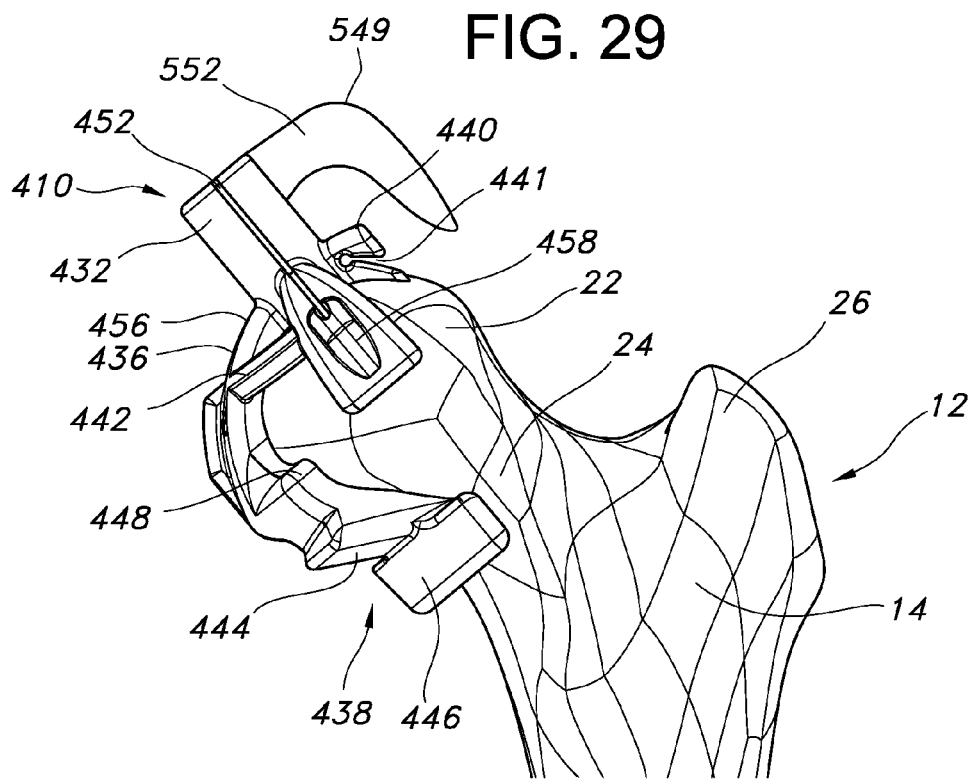

FIGS. 26-30 show various forms of alignment structures 549 that can be used to help align the guide 410. Such structures 549 can include an axis or plane that is generally coplanar to a bore guide 434 in the guide 410. Such alignment structures 549 can be included in any of the embodiments disclosed in this document to help allow the surgeon to gain additional information about placement of the guide and, thus orientation of a bore in femoral head 22 to be formed using the guide, in varus/valgus and/or version, among other reference planes and directions. FIGS. 26, 27a and 27b show embodiments of such an alignment structure 549 in the form of a stylus 550 that allows the guide 410 to enhance proximal neck visualization, in addition to the distal arm 436 boss 458 alignment rod hole and anterior/posterior arm 436 boss 458 alignment rod holes. In some instances, there may be better visualization of the proximal neck. Alternatively, as shown in FIG. 29, alignment structure 549 can take the form of a lateral projection 552 formed on the central member 432 to hold a proximal alignment rod 554;

alternatively, as shown in FIG. 30 the projection 552 itself can be used to visually align the guide 410 with the femoral neck 24. As discussed above, bosses 458 may include structures similar to projection 552.

Figure 31:
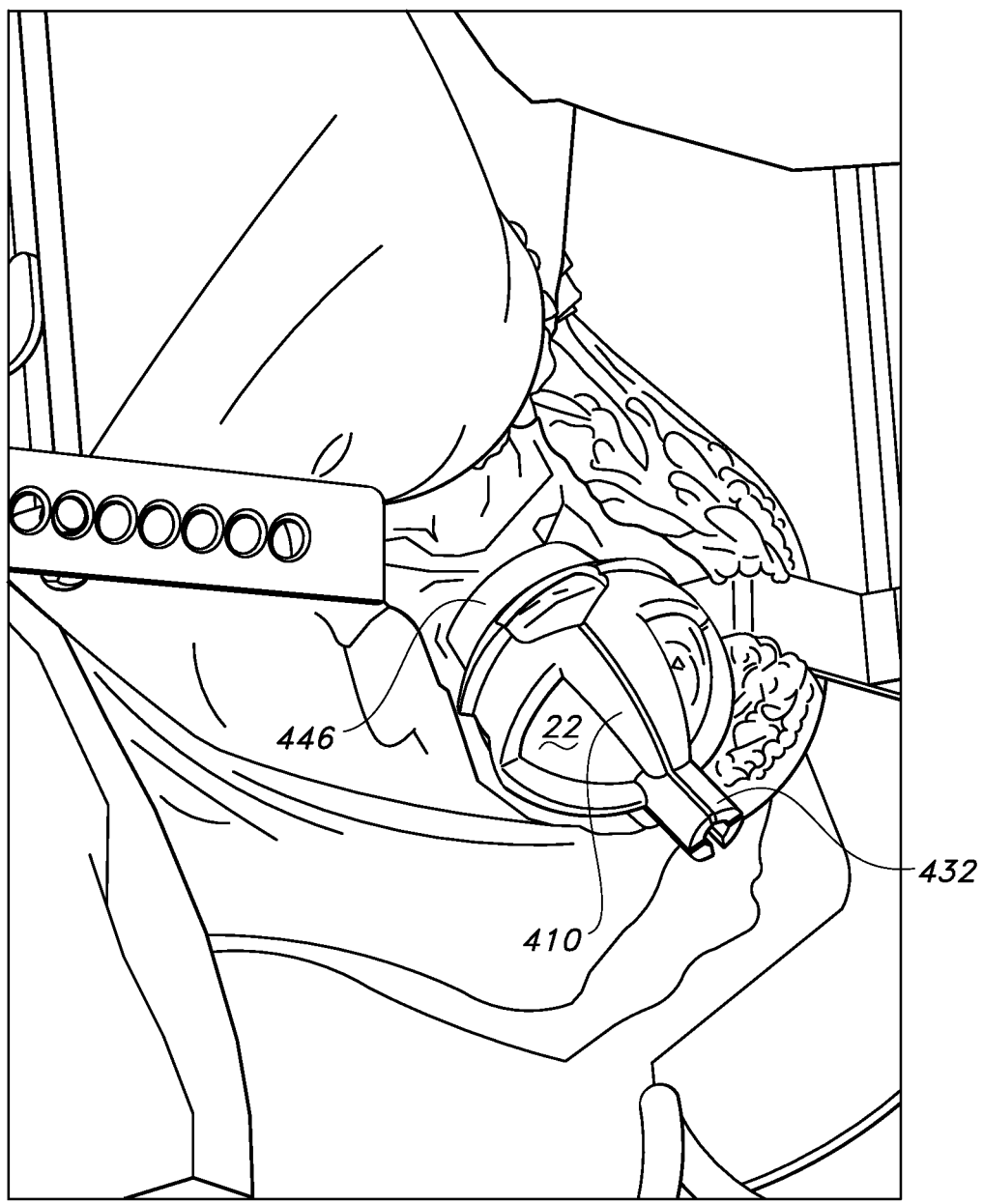
FIGS. 31 and 32 are views of posterior approach installation of a patient specific alignment guide according to an embodiment of the invention.
Figure 32:
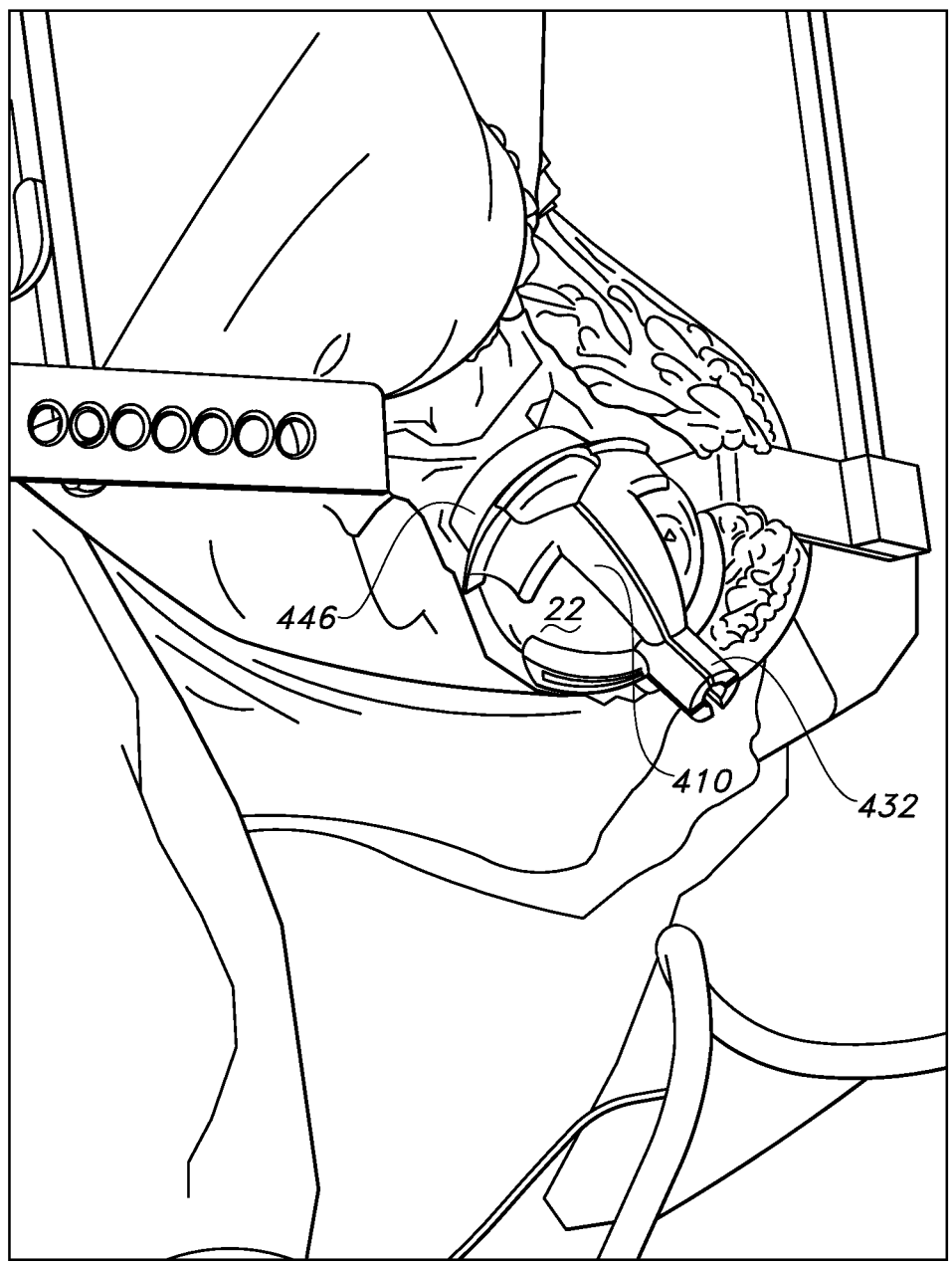
Figure 33:
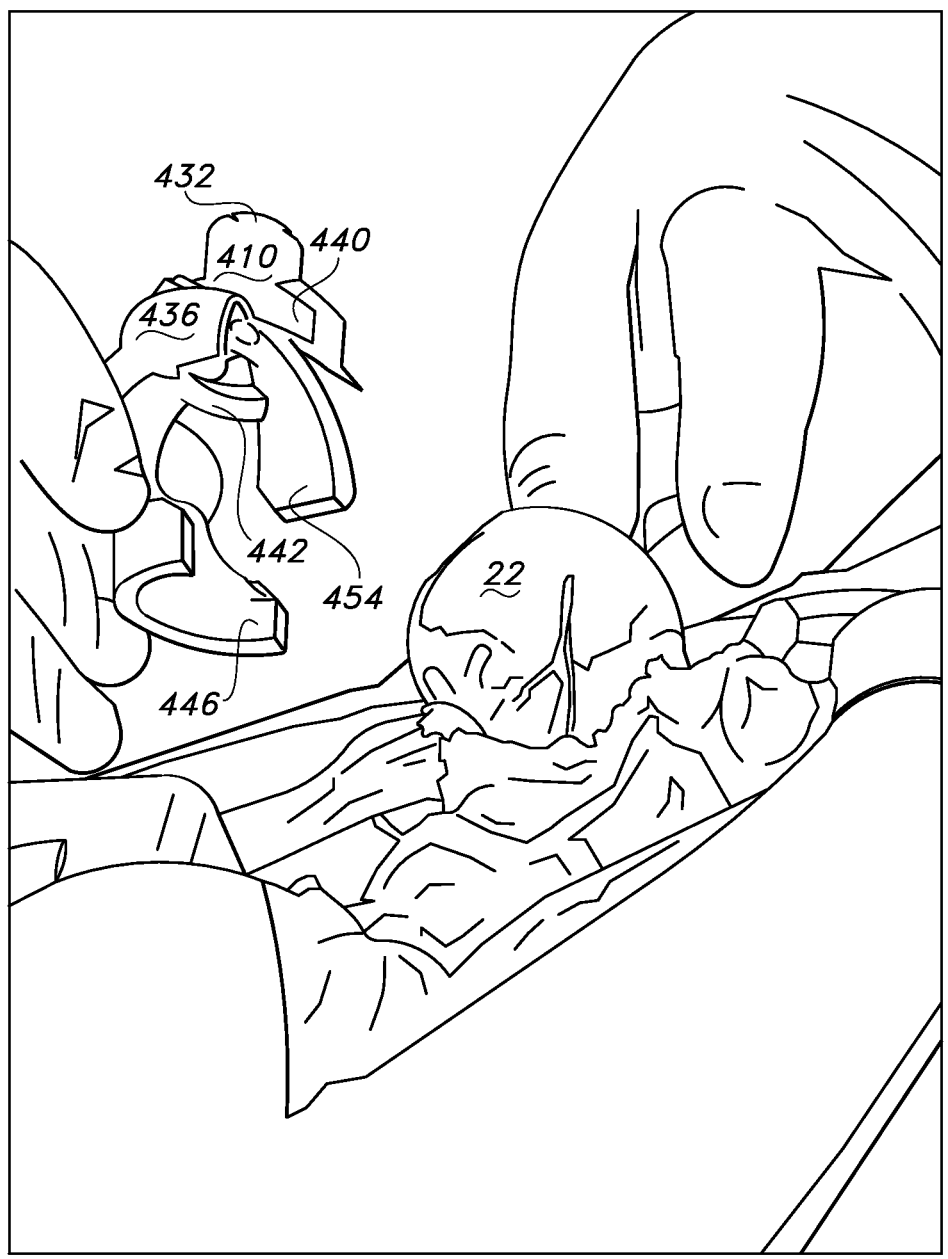
FIGS. 33 and 34 are views of an anterior approach installation of a patient specific alignment guide according to an embodiment of the invention.
Figure 34:
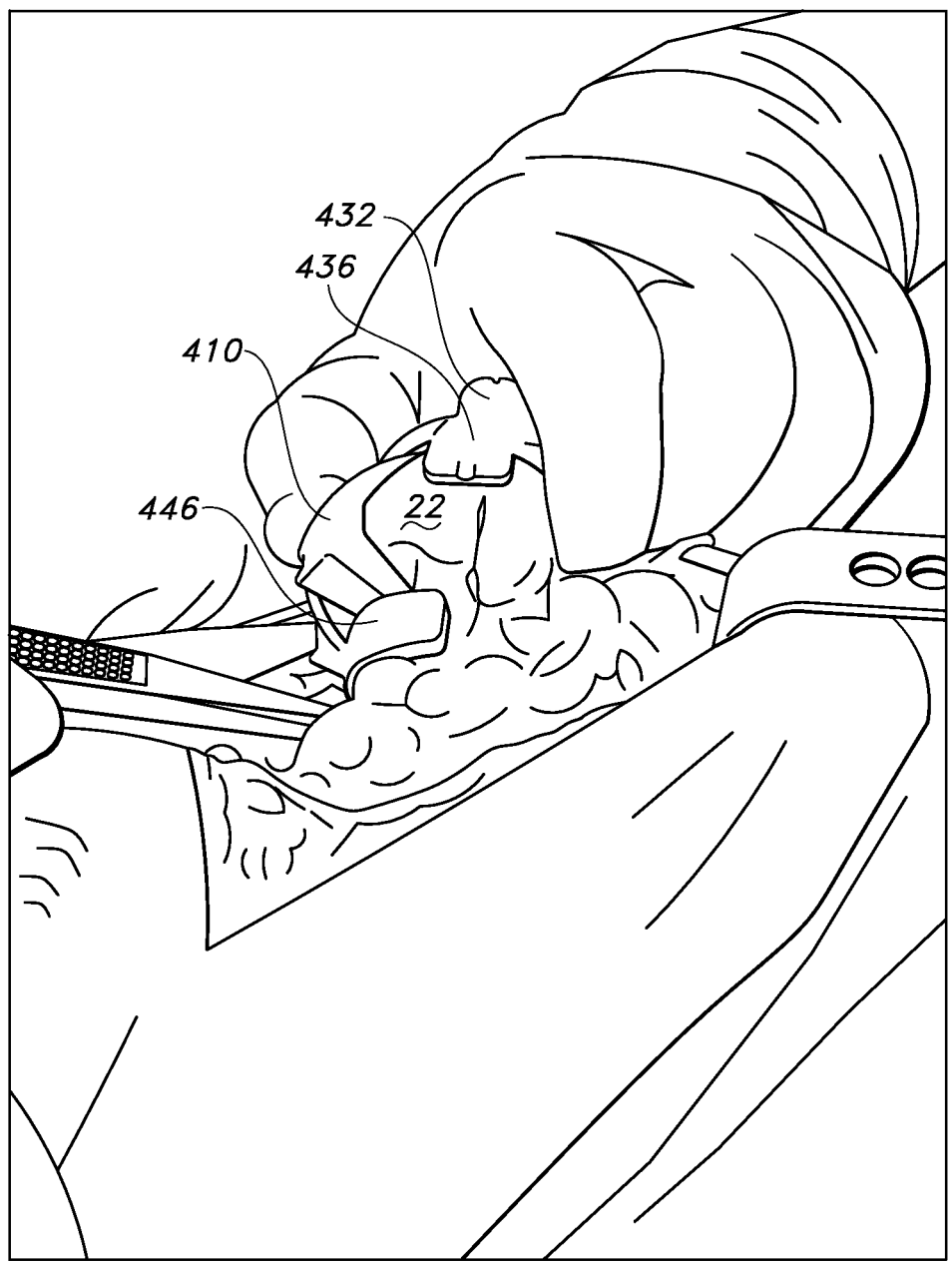

FIGS. 31 and 32 show a guide 410 in the process of being installed on a femur 12 in a posterior approach surgery. FIGS. 33 and 34 show a guide 410 being installed on a femur 12 in a direct anterior approach surgery. Guide 410, and other guides according to various embodiments of the invention are suitable not only for posterior and direct anterior surgical approaches, but also postero-lateral approaches. To the best of the inventors' knowledge, guide 410 and other guides according to embodiments of the invention are the only ones that are suitable to direct anterior approaches because their minimal structural size and optimally located anatomical contacting portions presents minimal obtrusiveness when being positioned and installed on femur 12. The greater bulkiness, size and non optimally located anatomical contacting portions of other prior art femoral head resection guides, by contrast, causes them to interfere with soft tissue and otherwise not be suitable for such minimally invasive, including direct anterior approach, surgery. As mentioned above, split 437 also assists in a similar way, in order to allow the guide 410 to be extracted from a pin in the femur without having to be extracted axially over the end of the pin.

In surgery, the surgeon forms an incision, whether in the posterior, direct anterior or postero-lateral approach and exposes the femoral head 22. The guide 410 (or other suitable guide according to other embodiments of the invention) is then located and snapped onto the head 22 and the neck 24 preferably by hooking an underside of the neck member 446 and rolling the guide 410 onto the head by pivoting in a proximolateral direction. Ease of installing these guides is enhanced by their reduced size and ability to be snapped on to the bone from generally a single direction such as, for instance, a generally distal direction. The guide 410 can be placed over the femoral head 22 from inferior to superior and should snap into place. Checks can be made to ensure that the guide 410 is properly seated against the bone by confirming contact on the femoral head 22 and neck 24. The window 450 allows inspection of contact surfaces. The guide can be adjusted slightly by rotating about the femoral neck 24 such that the medial indica 452 on the distally extending arm 436 aligns with the center line on the inferior aspect of the femoral neck 24. Guide wires can be placed in bosses 458 on anterior, posterior and/or distally extending arms 436 in order to verify prescribed version and valgus alignment. The sleeve cutter reference ring 442 can provide a reference for the smallest femoral component that may not notch the femoral neck 24. Once satisfied with the guide's positioning, the surgeon can place a pivot rod in the bore guide 434 and use a stylus on the pivot rod to check that it does not interfere with any part of the exposed femoral neck 24 when dialed to the proper size and rotated. After all checks have been completed, the guide 410 can be held in place and a guidewire drilled through the pivot rod that is located in bore guide 434 or the axial bore in the femoral head 22 can otherwise be formed as desired using the bore guide 434. The guide 410 can be easily removed or withdrawn distally or otherwise by using the split 437 in finger 440 to withdraw guide 410 over the pivot rod and/or the pin alone. Other checks can be performed as desired, the femoral head resected using an appropriate sleeve cutter and the axial bore formed with guide 410 an implant installed, the hip reassembled and the surgery completed.

FIG. 35 shows an anterior view of another alternative embodiment of the invention in the form of guide 510. Guide 510 includes a central member 532 that includes several bore guides 534. The central member is generally planar in shape to accommodate bore guides 532 along a number of axes to allow formation of a bore in femoral head 22 in corresponding directions. This configuration allows, therefore, multiple options for adjusting orientation of the bore in femoral head 22 in varus/valgus when the guide 510 has been aligned on femoral head 22. FIG. 35 also shows guide wires 535 extending from bore guides 534, although in practice, it is more likely the case that only one bore guide 534 is ultimately selected and used. Guide 510 includes a shell 536, cradle 538, head outer side member 544, and neck member 546; some or all of the interior surfaces of any or all of these components may be formed in a patient specific manner as disclosed above. Guide 510 also includes windows 551 to allow navigation on femoral head 22.

FIG. 36 shows an anterior view of another alternative embodiment of the invention in the form of guide 610. Guide 610 includes a central member 632 that is generally planar in shape to include a plurality of bore guides 634 in a manner similar to guide 510. Additionally, guide 610 includes one or more bosses 658 which can be oriented in any desired direction on outer surface 656 of guide 610 and, if desired, accept a stylus 660 to help the surgeon orient the guide 610 on femoral head 22. As is the case with guide 510, guide 610 includes a shell 636, a cradle 638, head underside member 644, neck member 646; some or all of the interior surfaces of any or all of these components may be formed in a patient specific manner as disclosed above. Windows 650 allow for navigation of guide 610 on the femoral head 22.

FIG. 37 shows an anterior view of another alternative embodiment of the invention in the form of guide 710. Guide 710 includes a central member 732 that is generally planar in shape to include a plurality of bore guides 734 in a manner similar to guides 510 and 610. As is the case with 510 and guide 610, guide 710 includes a shell 737, a cradle 738, a head underside member 644, a neck member 646; some or all of the interior surfaces of any or all of these components may be formed in a patient specific manner as disclosed above. Windows 750 allow for navigation on the femoral head 22.

FIG. 38 shows an anterior-medial view of another alternative embodiment of the invention in the form of guide 810. Guide 810 includes a central member 832 that is generally cruciform in shape to include a plurality of bore guides 834. Bore guides 834 may be arranged at various angles along a varus/valgus plane to allow multiple options for formation of bores in femur 22 in varus/valgus when the guide 810 has been positioned. The central member 832 also includes an orthogonal portion to form the cross member of the cruciform to allow multiple options for formation of bores in femoral head 22 in version. Guide 810 includes one or more bosses 858 which can be oriented in any desired direction on outer surface 856 of guide 810 and, if desired, accept a stylus 860 to help the surgeon orient the guide 810 on femoral head 22. As is the case with guides 510, 610 and 710, the structure includes a shell 836, a cradle 838, a head underside member 644 and a neck member 646; some or all of the interior surfaces of any or all of these components may be formed in a patient specific manner as disclosed above. Windows 850 allow for navigation on the femoral head 22.

All embodiments of the guides shown in the figures may be used in any hip approach. For example, they may be used in anterolateral, direct-lateral, posterolateral, direct-anterior, and any variations on these approaches. The profile of the guides is meant generally not to disturb soft tissue of the joint and minimize disruptions to blood flow around the joint. Cut outs may be oriented around the guide to avoid neck impingement and to give the surgeon a window to see the guide is properly seated on bone. While the embodiments have been disclosed individually, many portions of each embodiment may be interchangeable and combined to form an alignment guide in an alternate embodiment.

In view of the foregoing, it will be seen that the several advantages of embodiments of the invention are achieved and attained.

The embodiments were chosen and described in order to explain the principles of embodiments of the invention and their practical application to thereby enable others skilled in the art to best utilize such embodiments and with various modifications as are suited to the particular use contemplated.

As various modifications could be made in the constructions and methods herein described and illustrated without departing from the scope of inventions and embodiments contemplated herein, it is intended that all matter contained in the foregoing description or shown in the accompanying drawings shall be interpreted as illustrative rather than limiting. Thus, the breadth and scope of the invention should not be limited by any of the above-described exemplary embodiments, but should be defined only in accordance with the following claims appended hereto and their equivalents.

What is claimed is:

1. An alignment guide configured to conform to portions of a femoral neck and a femoral head of a femur of a specific patient, the guide comprising:
    a central member that includes a bore guide, the bore guide configured to guide formation of a bore along a target axis in the femoral head of the specific patient;
    a plurality of arms extending from the central member, each arm having an inner surface, a portion of the inner surface of each arm configured to contact a portion of the femoral head of the specific patient;
    a curved sleeve cutter guide connected to at least one of the arms, the sleeve cutter guide configured to indicate a potential location of a surface formed by a sleeve cutter;
    a head underside member connected to at least one of the arms, the head underside member including an inner surface; and
    a neck member connected to the head underside member, the neck member including an inner surface, wherein:
        a conforming portion of at least one of the head underside member inner surface and the neck member inner surface is configured to contact a corresponding portion of the femur of the specific patient; and
        the plurality of arms, the head underside member and the neck member are configured to cause the alignment guide to grip the specific patient's femoral head during formation of the bore in the specific patient's femoral head, and to be removably retained in place on the specific patient's femoral head in order to orient the bore guide to guide formation of the bore along the target axis in the specific patient's femoral head when the conforming portion of the head underside member inner surface or the neck member inner surface contacts the corresponding portion of the femur of the specific patient.

2. An alignment guide according to claim 1 configured to snap on to the femur of the specific patient.

3. An alignment guide according to claim 1 further comprising indicia located on an outer surface of the guide, the indicia oriented and configured to indicate alignment of the guide relative to varus/valgus angulation or version angulation.

4. An alignment guide according to claim 1 further comprising a slit formed in the central member and the bore guide, the slit configured to permit the guide to be withdrawn from a structure extending from the femoral head of the specific patient.

5. An alignment guide according to claim 1 further comprising a boss formed on the outer surface of the guide, the boss including structure adapted to receive a stylus for aid in alignment of the guide relative to the femoral head.

6. An alignment guide according to claim 1 further comprising two head underside members, the head underside members connected to at least one of the arms and to at least one neck member to define a window.

7. An alignment guide according to claim 4 further comprising a finger extending from the central member, the finger including an inner surface, conforming portions of the inner surface of the finger configured to contact corresponding portions of the femoral head of the specific patient.

8. An alignment guide according to claim 7 wherein the finger is bifurcated and configured to permit the guide to be withdrawn from a structure extending from the femoral head of the specific patient.

9. An alignment guide according to claim 1 wherein the central member, arms, head underside member, and neck member are configured to feature minimal size sufficient to snap on to the femoral head and to grip the femoral head while conforming to the femoral head, whereby the alignment guide is configured to be installed and withdrawn in anterior approach hip surgery on the specific patient.

10. An alignment guide according to claim 1 wherein at least one arm is configured to extend distally from the central member when the guide is installed on the femur of the specific patient, and another arm is configured to extend anteriorly or posteriorly from the central member when the guide is installed on the femur of the specific patient.

11. An alignment guide according to claim 1 wherein substantially all of the inner surfaces of the arms, the head underside member and the neck member include conforming portions configured to contact corresponding portions of the femur of the specific patient.

12. An alignment guide according to claim 1 further comprising an alignment structure connected to the alignment guide, the alignment structure including a plane or axis that is substantially coplanar to a longitudinal axis of the bore guide.

13. An alignment guide configured to conform to portions of a femoral neck and a femoral head of a femur of a specific patient, the guide comprising:
    a central member that includes a bore guide, the bore guide configured to guide formation of a bore along a target axis in the femoral head of the specific patient;
    at least two arms extending from the central member, each arm having an inner surface, a portion of the inner surface of each arm configured to contact a portion of the specific patient's femur, wherein a first of the arms is configured to extend distally from the central member when the guide is installed on the specific patient's femur, and a second of the arms is configured to extend from the central member in a direction different than the direction in which the first arm extends;

a curved sleeve cutter guide connected to the alignment guide, the sleeve cutter guide configured to indicate potential location of a surface formed by a sleeve cutter;

a head underside member connected to at least one of the arms, the head underside member including an inner surface;

a neck member connected to the head underside member, the neck member including an inner surface, wherein at least one of the head member inner surface and the neck member inner surface includes a conforming portion that is configured to contact a corresponding portion of the specific patient's femur; and a slit formed in the central member and the bore guide, the slit configured to permit the guide to be withdrawn from a structure extending from the patient's femoral head, wherein:

all parts of the alignment guide are configured to be sufficiently small and nonobtrusive relative to the specific patient's anatomy so as to permit the guide to be usable in anterior approach hip resurfacing surgery on the specific patient; and the guide is configured to grip the specific patient's femoral head in removable fashion when placed on the specific patient's femoral head in order to orient the bore guide for formation of a bore along the target axis in the specific patient's femoral head when the conforming portion of the head underside member inner surface or the neck member inner surface contacts the corresponding portion of the femur of the specific patient.

14. An alignment guide according to claim 13 further comprising indicia on the alignment guide, the indicia configured to aid in orienting the alignment guide relative to the specific patient's anatomy in at least one of the following alignment directions:

varus/valgus, and version.

15. An alignment guide according to claim 13 further comprising a boss on the guide, the boss including structure configured to receive a stylus.

16. An alignment guide according to claim 13 further comprising two head underside members, the head underside members connected to at least one arm and at least one neck member to define at least one window.

17. An alignment guide according to claim 13 further comprising a finger extending from the central member, the finger including an inner surface, conforming portions of the inner surface of the finger configured to contact corresponding portions of the femoral head of the specific patient.

18. An alignment guide according to claim 17 wherein the finger is bifurcated and configured to permit the guide to be withdrawn from a structure extending from the femoral head of the specific patient.

19. An alignment guide according to claim 13 wherein substantially all of the inner surfaces of the arms, the head underside member and the neck member include conforming portions configured to contact corresponding portions of the femur of the specific patient.

20. An alignment guide according to claim 13 further comprising an alignment structure coupled to the alignment guide, the alignment structure including an axis or plane that is substantially coplanar to a longitudinal axis of the bore guide.

* * * * *